United States Patent
Gong et al.

(10) Patent No.: US 11,987,802 B2
(45) Date of Patent: May 21, 2024

(54) ONCOLYTIC VIRUS VECTOR AND APPLICATION THEREOF

(71) Applicant: SHANGHAI YUNYING BIOPHARMACEUTICAL TECHNOLOGY CO., LTD., Shanghai (CN)

(72) Inventors: Ziying Gong, Shanghai (CN); Daoyun Zhang, Shanghai (CN); Yonghua Sun, Shanghai (CN); Yi Wang, Shanghai (CN); Nan Shi, Shanghai (CN); Jun Zhu, Shanghai (CN); Miao Ding, Shanghai (CN)

(73) Assignee: SHANGHAI YUNYING BIOPHARMACEUTICAL TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 18/349,983

(22) Filed: Jul. 11, 2023

(65) Prior Publication Data

US 2024/0002884 A1    Jan. 4, 2024

Related U.S. Application Data

(63) Continuation of application No. PCT/CN2021/098139, filed on Jun. 3, 2021.

(51) Int. Cl.
*C12N 7/01* (2006.01)
*C07K 14/035* (2006.01)
*C07K 14/705* (2006.01)
*C07K 16/28* (2006.01)
*C12N 15/86* (2006.01)

(52) U.S. Cl.
CPC .......... *C12N 15/86* (2013.01); *C07K 14/035* (2013.01); *C07K 14/70503* (2013.01); *C07K 14/70532* (2013.01); *C07K 16/2809* (2013.01); *C12N 2710/16043* (2013.01)

(58) Field of Classification Search
None
See application file for complete search history.

(56) References Cited

FOREIGN PATENT DOCUMENTS

| | | |
|---|---|---|
| CN | 108064305 A | 5/2018 |
| CN | 108635380 A | 10/2018 |
| CN | 109789177 A | 5/2019 |
| CN | 112840020 A | 5/2021 |
| WO | 2018170133 A1 | 9/2018 |
| WO | 2020052551 A1 | 3/2020 |

OTHER PUBLICATIONS

International Search Report in PCT/CN2021/098139 mailed on Dec. 27, 2021, 11 pages.
Written Opinion in PCT/CN2021/098139 mailed on Dec. 27, 2021, 9 pages.
First Office Action in Chinese Application No. 202180001529.3 mailed on Jul. 5, 2022, 16 pages.
Decision to Grant a Patent in Chinese Application No. 202180001529.3 mailed on Nov. 2, 2022, 6 pages.

*Primary Examiner* — Michael D Pak
(74) *Attorney, Agent, or Firm* — METIS IP LLC

(57) ABSTRACT

The embodiments of the present disclosure may provide an oncolytic virus vector and an application thereof. The oncolytic virus vector may comprise a recombinant nucleic acid. The recombinant nucleic acid may include: (i) a first nucleic acid fragment encoding a soluble PD-1 molecule; (ii) a second nucleic acid fragment encoding a CD86 molecule; and (iii) a third nucleic acid fragment encoding an antibody to a CD3 molecule.

9 Claims, 9 Drawing Sheets
Specification includes a Sequence Listing.

ONCOLYTIC VIRUS VECTOR AND APPLICATION THEREOF

CROSS-REFERENCE TO RELATED APPLICATION

This application is a continuation of International Application NO. PCT/CN2021/098139, filed on Jun. 3, 2021, the entire contents of which are incorporated herein by reference.

SEQUENCE LISTING

The instant application contains a Sequence Listing which has been submitted electronically in XML format and is hereby incorporated by reference in its entirety. The XML copy, created on Apr. 27, 2023, is named "Sequence Listing-20699-0007US00" and is 18,925 bytes in size.

TECHNICAL FIELD

The present disclosure relates to the field of biotechnology, and in particular, to an oncolytic virus vector comprising a recombinant nucleic acid and an application thereof.

BACKGROUND

At present, viral drugs represented by oncolytic viruses are playing an increasingly important role in the treatment of tumors. The oncolytic viruses refer to a class of viruses that can effectively infect and destroy cancer cells. The oncolytic viruses replicate and proliferate in cancer cells and release new infectious virus particles to infect and destroy other cancer cells. The oncolytic virus also produce proteins that have effects on cancer cells to affect a tumor microenvironment and stimulate a host to generate anti-tumor immune response(s) or directly dissolve the tumor. Due to the properties of the oncolytic viruses, such therapies are usually administered systemically or locally to treat primary and metastatic tumors. When cancer cells rupture and die under the infection of the oncolytic virus, newly generated virus particles are released and further infect surrounding cancer cells. The oncolytic viruses not only kill tumors cells directly, but also stimulate the body's immune response(s) and enhance an anti-tumor effect. In addition to being used alone, the oncolytic viruses are also administered in combination with other anti-cancer drugs. In addition, the oncolytic virus can also be recombined with foreign gene(s) that are beneficial for the treatment of cancer. In this way, on the one hand, such viruses can exert oncolytic effects through oncolytic protein(s), and on the other hand, an anti-cancer effect of other drugs can also be obtained. Therefore, in order to achieve better therapeutic results against cancer, there is a continuing need for an oncolytic virus that includes a recombinant nucleic acid.

SUMMARY

One aspect of the present disclosure may provide an oncolytic virus comprising a recombinant nucleic acid. The recombinant nucleic acid may include: (i) a first nucleic acid fragment encoding a soluble PD-1 molecule; (ii) a second nucleic acid fragment encoding a CD86 molecule; and (iii) a third nucleic acid fragment encoding an antibody to a CD3 molecule.

In some embodiments, a similarity between the first nucleic acid fragment and a sequence shown in SEQ ID NO: 1 may be greater than or equal to 90%.

In some embodiments, a similarity between the second nucleic acid fragment and a sequence shown in SEQ ID NO: 2 may be greater than or equal to 90%.

In some embodiments, a similarity between the third nucleic acid fragment and a sequence shown in SEQ ID NO: 3 may be greater than or equal to 90%.

In some embodiments, the recombinant nucleic acid may further include: (iv) a fourth nucleic acid fragment encoding a US11 protein.

In some embodiments, a similarity between the fourth nucleic acid fragment and a sequence shown in SEQ ID NO: 4 may be greater than or equal to 90%.

In some embodiments, the oncolytic virus may belong to a genus Herpes simplex virus.

In some embodiments, the oncolytic virus may be an HSV-1 virus, and a similarity between the recombinant nucleic acid and a sequence shown in SEQ ID NO: 5 may be greater than or equal to 80%.

In some embodiments, a recombinant sequence may include at least one of a nucleic acid fragment encoding a cytokine, a nucleic acid fragment encoding a molecule that facilitates the oncolytic virus to target and infect cancer cells, a nucleic acid fragment encoding an anti-angiogenic factor, and a nucleic acid fragment encoding a matrix metalloproteinase.

One aspect of the present disclosure may provide an oncolytic virus comprising a recombinant nucleic acid. The recombinant nucleic acid may include (i) a first nucleic acid fragment encoding a soluble PD-1 molecule; (ii) a second nucleic acid fragment encoding a CD86 molecule; (iii) a third nucleic acid fragment encoding an antibody to a CD3 molecule; and (iv) a fourth nucleic acid fragment encoding a US11 protein.

In some embodiments, the oncolytic virus may be an HSV-1 or an HSV-2 virus, and the fourth nucleic acid fragment may include an exogenous nucleic acid fragment inserted into the recombinant nucleic acid.

In some embodiments, the oncolytic virus may be the HSV-1 virus, and a similarity between the recombinant nucleic acid and a sequence shown in SEQ ID NO: 5 may be greater than or equal to 80%.

In some embodiments, when the oncolytic virus acts on human non-small cell lung cancer cells, human liver cancer cells, human breast cancer cells, or human pancreatic cancer cells at a multiplicity of infection of 2 in a culture environment, at least 70%, 90%, 60%, or 40% of the cancer cells may be caused to die within 48 hours, respectively.

In some embodiments, when the oncolytic virus acts on human non-small cell lung cancer cells, human liver cancer cells, human breast cancer cells, or human pancreatic cancer cells at a multiplicity of infection of 1 in a culture environment, at least 70%, 80%, 60%, or 40% of the cancer cells may be caused to die within 48 hours, respectively.

In some embodiments, when the oncolytic virus is injected into a non-small cell lung cancer tumor with one injection at a dose of $8\times10^6$ pfu, at least 60% of a tumor volume may be reduced within 100 days; or when the oncolytic virus is injected into the non-small cell lung cancer tumor with three injections at the dose of $8\times10^6$ pfu, at least 80% of the tumor volume may be reduced within 100 days.

In some embodiments, when the oncolytic virus is injected into a subject suffering from colon cancer at a dose of at least $3\times10^6$ pfu, a survival period of the subject may be extended.

One aspect of the present disclosure may provide a composition for treating cancer. The composition may include any one of the above-mentioned oncolytic viruses and a pharmacologically acceptable vector or excipient.

In some embodiments, the cancers may include melanoma, lung cancer, leukemia, gastric cancer, ovarian cancer, pancreatic cancer, breast cancer, prostate cancer, bladder cancer, rectal cancer, liver cancer, cervical cancer, or osteosarcoma.

In some embodiments, the cancers may include lung cancer, liver cancer, breast cancer, pancreatic cancer, or colon cancer.

One aspect of the present disclosure may provide a composition for treating non-small cell lung cancer or colon cancer. The composition may include any one of the above-mentioned oncolytic virus and a pharmacologically acceptable vector or excipient.

One aspect of the present disclosure may provide an application of any one of the above-mentioned oncolytic virus in the preparation of a drug for treating cancer.

In some embodiments, the cancers may include melanoma, lung cancer, leukemia, gastric cancer, ovarian cancer, pancreatic cancer, breast cancer, prostate cancer, bladder cancer, rectal cancer, liver cancer, cervical cancer, or osteosarcoma.

In some embodiments, the cancers may include lung cancer, liver cancer, breast cancer, pancreatic cancer, or colon cancer.

One aspect of the present disclosure may provide an application of any one of the above-mentioned oncolytic virus in the preparation of a drug for treating non-small cell lung cancer or colon cancer.

One aspect of the present disclosure may provide a method for treating cancer. The method may include: administering an effective dose of the above-mentioned composition to a subject suffering from the cancer.

In some embodiments, the cancers may include melanoma, lung cancer, leukemia, gastric cancer, ovarian cancer, pancreatic cancer, breast cancer, prostate cancer, bladder cancer, rectal cancer, liver cancer, cervical cancer, or osteosarcoma.

In some embodiments, the cancers may include lung cancer, liver cancer, breast cancer, pancreatic cancer, or colon cancer.

In some embodiments, the subject may be a mammal.

In some embodiments, a ratio of an amount of the oncolytic virus in the effective dose of the composition to a body weight of the subject may be in a range of $1 \times 10^6$ pfu/kg-$2 \times 10^6$ pfu/kg.

In some embodiments, a ratio of an amount of the oncolytic virus in the effective dose of the composition to a body weight of the subject may be in a range of $1.30 \times 10^6$ pfu/kg-$1.70 \times 10^6$ pfu/kg.

In some embodiments, the administering an effective dose of the composition to a subject suffering from cancer may include: administering the composition to the subject by injection.

In some embodiments, the administering the composition to the subject by injection may include: injecting the composition into the subject at a site in or near a tumor.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, and wherein.

DETAILED DESCRIPTION

Figure 1:
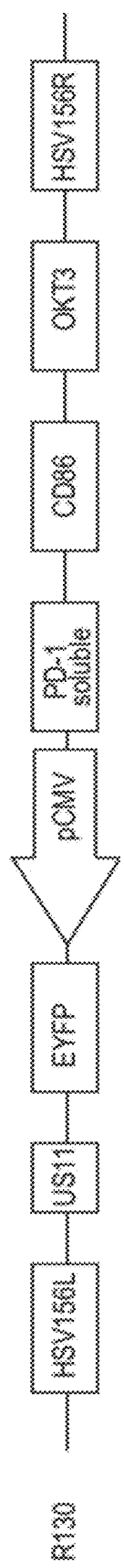
FIG. 1 is a schematic diagram illustrating a vector plasmid structure of a recombinant oncolytic virus according to some embodiments of the present disclosure.

The technical solutions of the present disclosure embodiments will be more clearly described below, and the accompanying drawings that need to be configured in the description of the embodiments will be briefly described below. Obviously, the drawings described below are only some examples or embodiments of the present disclosure. Those skilled in the art, without further creative efforts, may apply the present disclosure to other similar scenarios according to these drawings. Unless obviously obtained from the context or the context illustrates otherwise, the same numeral in the drawings refers to the same structure or operation.

As shown in the present disclosure and claims, unless the context clearly prompts the exception, "a", "one", and/or "the" is not specifically singular, and the plural may be included. It will be further understood that the terms "comprise," "comprises," and/or "comprising," "include," "includes," and/or "including," when used in the present disclosure, only suggest the inclusion of clearly identified steps and elements, and these steps and elements do not constitute an exclusive list, and the method or device may also contain other steps or elements.

As shown in the present disclosure and claims, unless the context clearly prompts the exception, the terms "comprise," "comprises," and/or "comprising," "include," "includes,"

and/or "including," when used in the present disclosure, may be understood as implying inclusion of stated elements, but do not preclude the presence or addition of one or more other steps and elements thereof.

The following are definitions of some terms used in the present disclosure.

As used in the present disclosure, an "subject" (also referred to as "individual" or "subject") may be an individual who is treated with an oncolytic virus or composition of the present disclosure. In some embodiments, the subject may be a vertebrate. The vertebrate may include a fish (e.g., shark), an amphibian (e.g., frog, toad, giant salamander), a reptile (e.g., turtle, snake, lizard), a bird (e.g., ostrich), a mammal, or the like. In some embodiments, the vertebrate may be a mammal. The mammal may include, but be not limited to, primates (including humans and non-human primates) and rodents (e.g., mice and rats). In some embodiments, the mammal may be a human. In some embodiments, the subject may have cancer and have received other treatments (e.g., chemotherapy) or have not received treatment.

The term "treating" (or "treatment") may refer to ameliorating or curing a disease (e.g., cancer) in the subject. In some embodiments, the treating may include alleviating, delaying, alleviating a severity of symptoms of cancer (e.g., reducing a tumor volume), reducing a frequency of the symptoms (e.g., pain) of the cancer, extending a survival time, increasing a survival rate, reducing a cancer cell viability, killing cancer cells, etc.

The term "effective dose" may refer to an amount of a composition sufficient to provide useful events or reduce adverse unfavorable events (e.g., a dose sufficient to treat a disease). In the present disclosure, the composition may include an oncolytic virus. An amount of the oncolytic virus in an effective dose of the composition may depend on a variety of factors including, but not limited to, a purpose of the treatment, a weight, gender, age, and general health of the subject, an administration route, an administration time, and a property of a disease to be treated.

The term "herpes simplex virus (HSV)" can be an enveloped, neurotropic, and double-stranded DNA virus. For example, the virus can be divided into herpes simplex virus type 1 (HSV-1) and herpes simplex virus type 2 (HSV-2).

The term "immune checkpoint inhibitor" may refer to an antibody that inhibits or blocks an inhibitory immune checkpoint molecule. The immune checkpoint may be a regulator and a modulator of an immune system, whose role is to prevent the immune system from attacking cells indiscriminately, which may be essential for self-tolerance.

The present disclosure may provide an oncolytic virus comprising a recombinant nucleic acid. The oncolytic virus may be a herpes simplex virus, e.g., an HSV-1 or HSV-2 virus. The recombinant nucleic acid may include a first nucleic acid fragment encoding a soluble programmed death-1 (sPD-1) molecule, a second nucleic acid fragment encoding CD86 molecule, a third nucleic acid fragment encoding an antibody to a cluster of differentiation 3 (CD3) molecule, and a fourth nucleic acid fragment encoding a US11 protein. The recombinant nucleic acid may also include a nucleic acid fragment encoding a cytokine, a nucleic acid fragment encoding a molecule that facilitates the oncolytic virus to target and infect cancer cells, a nucleic acid fragment encoding an anti-angiogenic factor, a nucleic acid fragment encoding a matrix metalloproteinase, or the like, or any combination thereof.

The present disclosure may also provide a composition for treating cancer. The composition may include any one of the above-mentioned oncolytic virus and a pharmacologically acceptable vector or excipient. The cancers capable of being treated by the composition may include, but be not limited to, melanoma, lung cancer, leukemia, gastric cancer, ovarian cancer, pancreatic cancer, breast cancer, prostate cancer, bladder cancer, rectal cancer, liver cancer, cervical cancer, osteosarcoma.

The present disclosure may also provide an application of the above-mentioned oncolytic virus in preparation of a drug for treating cancer. Specifically, the present disclosure may also provide an application of the above-mentioned oncolytic virus in preparation of a drug for treating lung cancer.

The present disclosure may further provide a method for treating cancer. The method may include administering an effective dose of the above-mentioned composition to a subject suffering from the cancer. The composition may be injected into the subject by injection, or the like. For example, the composition may be injected into a site in or near a tumor of the subject. In some embodiments, the composition may be injected into the subject in combination with other drugs (e.g., anti-cancer drugs).

The oncolytic virus and the composition thereof disclosed in the present disclosure may express proteins/antibodies that may activate T cells, express proteins/antibodies that may relieve T cell inhibition, which can improve an immune ability of the body, enhance an ability of the virus to escape from immune clearance of the host, and extend the survival time in the body, thereby inhibiting and killing the cancer cells, effectively reducing the survival rate of the cancer cells in the administration subject, effectively improve or slow down the symptoms of the cancer (such as reducing the tumor volume), and improve a survival ability of the subject.

One aspect of the present disclosure may provide an oncolytic virus (also referred to as "recombinant oncolytic virus") comprising a recombinant nucleic acid.

According to different genetic materials of viruses, oncolytic viruses may be divided into DNA-type oncolytic viruses and RNA-type oncolytic viruses. Exemplary DNA-type oncolytic viruses may include, but be not limited to, an adenovirus, a vaccinia virus, a parvovirus, a herpes simplex virus, or the like. Exemplary RNA-like oncolytic viruses may include, but be not limited to, a reovirus, a polio virus, a seneca valley virus, or the like.

In some embodiments of the present disclosure, the oncolytic virus may be HSV, which belongs to the family Herpesviridae, the genus Herpes simplex virus. The HSV may include HSV-1 and HSV-2. In some embodiments, the oncolytic virus may be an artificially engineered oncolytic virus. For example, an oncolytic virus encoding a neurotropic ICP34.5 (or γ-34.5) gene may be removed from a wild-type HSV-1 virus, thereby making it less neurotoxic, that is, an obtained oncolytic virus may be non-pathogenic/non-neurotoxic and oncolytic.

In some embodiments, the HSV-1 may be used as an oncolytic virus that selectively attacks cancer cells because it is easy to handle and relatively harmless in its natural state. By modifying the genes of the oncolytic virus (for example, the HSV-1), such as inserting other gene fragments that may inhibit and kill the cancer cells, the ability of the oncolytic virus to target and infect the cancer cells and/or the ability of the oncolytic virus to kill the cancer cells may be improved, so that the oncolytic virus may have a better anti-tumor treatment effect.

The recombinant nucleic acid may include one or more exogenous nucleic acid fragments. The exogenous nucleic acid fragments may include, but be not limited to, a nucleic acid fragment encoding an immune checkpoint inhibitor, a nucleic acid fragment encoding a co-stimulatory molecule, a nucleic acid fragment encoding an antibody to a surface antigen of effector cells, a nucleic acid fragment encoding a molecule that facilitates the oncolytic virus to evade or resist immune response(s) of the host, a nucleic acid fragment encoding the molecule that facilitates the oncolytic virus to target and infect cancer cells, the nucleic acid fragment encoding the cytokine, the nucleic acid fragment encoding the anti-angiogenic factor, a nucleic acid fragment encoding the matrix metalloproteinase, antisense or small RNAs that block or downregulate tumor-overexpressed proto-oncogenes and metabolic genes, a prodrug converting enzyme, or the like, or any combination thereof.

In some embodiments, the nucleic acid fragment encoding the immune checkpoint inhibitor may include, but be not limited to, a nucleic acid fragment encoding a soluble PD-1 molecule (i.e., the first nucleic acid fragment), a nucleic acid fragment encoding a PD-1 inhibitor, a nucleic acid fragment encoding a PD-L2 (or B7-DC, CD273) inhibitor, a nucleic acid fragment encoding a CTLA-4 inhibitor, a nucleic acid fragment encoding a LAG-3 inhibitor, a nucleic acid fragment encoding a TIM-3 inhibitor, a nucleic acid fragment encoding a neuropilin inhibitor, a nucleic acid fragment encoding a CCR4 inhibitor, a nucleic acid fragment encoding a TIGIT (or Vsig9, Vstm3, WUCAM) inhibitor, a nucleic acid fragment encoding a VISTA (or Dies1) inhibitor, or the like, or a combination thereof.

In some embodiments, the co-stimulatory molecule may refer to a molecule whose encoding may stimulate the proliferation of T cells or help activate the function of the T cells. The nucleic acid fragment encoding the co-stimulatory molecule may include, but be not limited to, a nucleic acid fragment encoding a B7 family, a nucleic acid fragment encoding CD27, a nucleic acid fragment encoding CD28, a nucleic acid fragments encoding CD70, a nucleic acid fragment encoding CD83, a nucleic acid fragment encoding CD134 (or OX-40), a nucleic acid fragment encoding CD134L (or OK-40L), a nucleic acid fragment encoding CD137 (or 41BB), a nucleic acid fragment encoding CD137L (or 41 BBL), a nucleic acid fragment encoding CD224, a nucleic acid fragment encoding GITR, a nucleic acid fragment encoding ICOS, or the like, or any combination thereof. In some embodiments, the nucleic acid fragment encoding the co-stimulatory molecule may include the nucleic acid fragment encoding the B7 family, including, but not limited to, a nucleic acid fragment encoding B7-1 (or CD80), a nucleic acid fragment encoding B7-2 (or CD86), a nucleic acid fragment encoding B7-H1 (or PD-L1, CD274), a nucleic acid fragment encoding ICOS-L (or CD275, B7-H2), a nucleic acid fragment encoding B7-H3 (or CD276), a nucleic acid fragment encoding B7-H4, a nucleic acid fragment encoding B7-DC (or PD-L2, CD273), or a nucleic acid fragment encoding BT3.1 (or CD277).

In some embodiments, the nucleic acid fragment encoding the antibody to the surface antigen of the effector cells may include a nucleic acid fragment encoding an antibody to a surface antigen of T cells and a nucleic acid fragment encoding an antibody to a surface antigen of B cells, such as a nucleic acid fragment encoding an antibody to a CD3 molecule (that is, the third nucleic acid fragment), a nucleic acid fragment encoding an antibody to a CD4 molecule, a nucleic acid fragment encoding an antibody to a CD5 molecule, a nucleic acid fragment encoding an antibody to a CD8 molecule, a nucleic acid fragment encoding an antibody to a CD45RO molecule, a nucleic acid fragment encoding an antibody to a CD20 molecule, a nucleic acid fragment encoding an antibody to a CD21 molecule, a nucleic acid fragment encoding an antibody to a CD45RA molecule, or the like, or any combination thereof.

The nucleic acid fragment encoding the molecule that facilitates the oncolytic virus to evade or resist immune response(s) of the host may include, but be not limited to, a nucleic acid fragment encoding US11 (i.e., the fourth nucleic acid fragment), a nucleic acid fragment encoding UL82, or the like, or any combination thereof.

The nucleic acid fragment encoding the molecule that facilitates the oncolytic virus to target and infect cancer cells may include, but be not limited to, a nucleic acid fragment encoding a CD86 molecule, or the like.

The nucleic acid fragment encoding the cytokine may include, but be not limited to, a nucleic acid fragment encoding GM-CSF, a nucleic acid fragment encoding G-CSF, a nucleic acid fragment encoding M-CSF, a nucleic acid fragment encoding IL-1, a nucleic acid fragment encoding IL-2, a nucleic acid fragment encoding IL-3, a nucleic acid fragment encoding IL-4, a nucleic acid fragment encoding IL-5, a nucleic acid fragment encoding IL-6, a nucleic acid fragment encoding IL7, a nucleic acid fragment encoding IL-8, a nucleic acid fragment encoding IL-10, a nucleic acid fragment encoding IL-12, a nucleic acid fragment encoding IL-13, a nucleic acid fragment encoding IL-15, a nucleic acid fragment encoding IL-18, a nucleic acid fragment encoding IL-21, a nucleic acid fragment encoding IL-23, a nucleic acid fragment encoding IFN-α, a nucleic acid fragment encoding IFN-γ, a nucleic acid fragment encoding TGF-β, a nucleic acid fragment encoding TNF-α, or the like, or any combination thereof.

The nucleic acid fragment encoding the anti-angiogenic factor may include, but be not limited to, a nucleic acid fragment encoding one or more interacting polypeptides that disrupt a cell type (e.g., endothelial cells (EC) and circulating endothelial progenitor cells, pericytes, vascular smooth muscle cells, and mesenchymal cells, including stem cells, and parenchymal cells), a nucleic acid fragment encoding one or more interacting polypeptides that disrupt a secreted factor (e.g., a vascular endothelial growth factor (VEGF), a fibroblast growth factor (FGF), a platelet-derived growth factor (PDGF), or angiogenin), or the like, or combinations thereof.

The nucleic acid fragment encoding the matrix metalloproteinase may include, but be not limited to, a matrix metalloproteinase 1 (MMP1), a matrix metalloproteinase 2 (MMP2), a matrix metalloproteinase 3 (MMP3), a matrix metalloproteinase 7 (MMP7), a matrix metalloproteinase 9 (MMP9), and a matrix metalloproteinase 12 (MMP12).

In some embodiments, the recombinant nucleic acid of the oncolytic virus may include the nucleic acid fragment encoding the immune checkpoint inhibitor, the nucleic acid fragment encoding the co-stimulatory molecule, the nucleic acid fragment encoding the antibody to the surface antigen of the effector cells, and the nucleic acid fragment encoding the molecule that facilitates the oncolytic virus to evade or resist immune response(s) of the host.

In some embodiments, the recombinant nucleic acid may include the first nucleic acid fragment encoding the soluble PD-1 molecule, the second nucleic acid fragment encoding the CD86 molecule, and the third nucleic acid fragment encoding the antibody to a CD3 molecule. Additionally or alternatively, the recombinant nucleic acid may include the fourth nucleic acid fragment encoding the US11 protein.

The soluble PD-1 molecule may be an extracellular region of a PD-1 immunosuppressive molecule, which may competitively bind to a ligand PD-L1 expressed by cancer cells, thereby releasing the inhibitory effect of the PD-1 and PD-L1 on T cells. Oncolytic viruses recombined with the soluble PD-1 molecule may effectively promote the immune response.

The CD3 molecule may be an important marker on a surface of the T cells and consists of five polypeptide chains, γ, δ, ε, ζ, and η. Antibodies to the CD3 molecule may specifically recruit the T cells expressing the CD3 molecule. Therefore, inserting a gene fragment capable of expressing the antibody to the CD3 molecule into a nucleic acid of the oncolytic virus may promote the activation and/or proliferation of the T cells and enhance the anti-tumor effect of the oncolytic virus. An exemplary nucleic acid fragment encoding the antibody to the CD3 molecule may include a nucleic acid fragment encoding OKT3, a nucleic acid fragment encoding L2K, a nucleic acid fragment encoding UCHT1, or the like, or any combination thereof. In some embodiments, the third nucleic acid fragment may be a nucleic acid fragment of OKT3.

Usually, the activation of the T cells may depend on two signals, one may be an antigenic peptide-MHC complex, which may be recognized by TCR. The second may be a co-stimulatory signal, which may affect the activation, proliferation, and cytokine secretion of the T cells. The B7 family may be the most important co-stimulatory molecule, among which CD80 and CD86 are homologous and may be important members of the B7 family. A nucleic acid fragment expressing OKT3 in the oncolytic virus may be used for specific recruitment of the T cells. A nucleic acid fragment expressing CD86 may further activate the T cells and enable the T cells to proliferate and differentiate. In some embodiments, the second nucleic acid fragment may also be a nucleic acid fragment of CD80.

US11 protein may interact with endogenous pattern recognition receptors RIG-I and MDA-5 and interfere with an interaction of RIG-I and MDA-5 with an adapter protein MAVS, thereby inhibiting the activation of an RLR-mediated innate immune downstream signaling pathway IRF3 and preventing generation of β interferon. The addition of the nucleic acid fragment encoding the US11 protein (i.e., the fourth nucleic acid fragment) may be used to enhance the ability of the oncolytic virus to evade the natural immune defense of the host and extend a retention time of the oncolytic virus in the body. In some embodiments, the fourth nucleic acid fragment may include an exogenous nucleic acid fragment inserted into the recombinant nucleic acid. For example, the exogenous nucleic acid fragment may be a nucleic acid fragment encoding an exogenous US11 protein (e.g., human, or animal). In some embodiments, the fourth nucleic acid fragment may include a non-exogenous nucleic acid fragment inserted into the recombinant nucleic acid, for example, a nucleic acid fragment encoding a US11 protein of the oncolytic virus.

In some embodiments, the similarity between the first nucleic acid fragment and a sequence shown in SEQ ID NO: 1 may be greater than or equal to 95%, 90%, 85%, 80%, etc. In some embodiments, the similarity between the second nucleic acid fragment and a sequence shown in SEQ ID NO: 2 may be greater than or equal to 95%, 90%, 85%, 80%, etc. In some embodiments, the similarity between the third nucleic acid fragment and a sequence shown in SEQ ID NO: 3 may be greater than or equal to 95%, 90%, 85%, 80%, etc. In some embodiments, the similarity between the fourth nucleic acid fragment and a sequence shown in SEQ ID NO: 4 may be greater than or equal to 95%, 90%, 85%, 80%, etc. In some embodiments, the similarity between the recombinant nucleic acid of the oncolytic virus and a sequence shown in SEQ ID NO: 5 may be greater than or equal to 95%, 90%, 85%, 80%, etc.

In some embodiments, the oncolytic virus may further include a fifth nucleic acid fragment whose encoding is used for screening the recombinant oncolytic virus, for example, an enhanced yellow fluorescent protein (EYFP). In some embodiments, one or more of the first nucleic acid fragment, the second nucleic acid fragment, the third nucleic acid fragment, the fourth nucleic acid fragment, and the fifth nucleic acid fragment may be linked to one or more expression control sequences. The one or more expression control sequences may include promoters, enhancers, polynucleotides (e.g., terminators), or the like, or combinations thereof. Exemplary promoters may include an SV40 promoter, a CMV promoter, an MSV promoter, an EF1 promoter, an MMLV promoter, a U6 promoter, an H1 promoter, or the like. Exemplary enhancers may include an SV40 enhancer, a CMV enhancer, or the like. The terminators may include SV40 PolyA, TK PolyA, BGH PolyA, or the like. For example, the first nucleic acid fragment may be operably linked to a promoter. As another example, the fifth nucleic acid fragment may be operably linked to the CMV promoter, the CMV enhancer, or the BGH PolyA.

In some embodiments, each exogenous nucleic acid fragment may be inserted into the nucleic acid of the oncolytic virus by one or more common manners in the art to obtain the above-mentioned recombinant nucleic acid, which may be not limited in the present disclosure. For example, one or more exogenous nucleic acid fragments may be inserted into a vector using ligases, fusion polymerase chain reaction (PCR) techniques, or the like, or a combination thereof. For example, the ligases may be sequentially used to ligate digested vectors and gene fragments to be inserted. As another example, the fusion PCR may be used to sequentially link various fragments together, and then fuse with the vector. Merely by way of example, the first and second vectors (such as plasmids) may be constructed, and a plurality of gene fragments (for example, 3 gene fragments) may be sequentially connected to the first vector using the ligases, other gene fragments may be sequentially connected to the second vector using the ligases, and the PCR may be used to obtain remaining gene fragments connected together, so as to be connected to the first vector. In some embodiments, the vector may be a nucleic acid of a wild-type oncolytic virus. For example, the vector may be a nucleic acid of a wild-type HSV-1 virus. In some embodiments, the vector may be a nucleic acid of an oncolytic virus deleted for one or more encoding genes (e.g., ICP34.5).

It should be noted that the present disclosure does not limit the sequence of each nucleic acid fragment in the recombinant nucleic acid. In some embodiments, the first, second, third, and fourth nucleic acid fragments may be respectively inserted into different sites of the nucleic acid of the oncolytic virus. In some embodiments, one or more of the first, second, third, and fourth nucleic acid fragments may be inserted into the same site in the nucleic acid of the oncolytic virus. In some embodiments, an insertion site of the above-mentioned nucleic acid fragments may be any suitable site in an encoding region of the nucleic acid of the oncolytic virus. For example, the insertion site of the above-mentioned nucleic acid fragments may be a position where one or more encoding genes (for example, ICP34.5) are deleted in the HSV-1 virus. In some embodiments, the exogenous nucleic acid fragments may be sequentially inserted into the same site or different sites in the nucleic acid of the oncolytic virus. The sequence of the exogenous nucleic acid fragments in the recombinant nucleic acid may be arbitrary. In some embodiments, the sequence (from 5' end to 3' end) of the nucleic acid fragments in the recombinant nucleic acid of the oncolytic virus may be the fourth nucleic acid fragment, the fifth nucleic acid fragment, the first nucleic acid fragment, the second nucleic acid fragment, and the third nucleic acid fragment.

One aspect of the present disclosure may provide a composition for treating cancer. The composition may include any one of the above-mentioned oncolytic virus and a pharmacologically acceptable vector or excipient.

The pharmacologically acceptable vectors may include coating layers, capsules, microcapsules, nanocapsules, or the like, or any combination thereof. It should be noted that the vector needs to be non-toxic and may not significantly affect the activity of key components (e.g., the above-mentioned oncolytic virus, molecules that promote anti-cancer effects expressed by the oncolytic virus, such as the soluble PD-1 molecule) in the composition. In some embodiments, the vector may protect the key components in the composition and reduce or avoid inactivation or decomposition of the key components under negative condition(s) (such as oxidation, denaturation caused by a strong acid or a strong alkali, etc.). For example, enzymes or a relatively low pH value in gastric juices may cause the key components to break down or become inactive. The vector may help maintain or enhance the efficacy of a pharmaceutical composition by protecting the key components in the composition.

In some embodiments, the vector may be used to control the release of the key components (e.g., the oncolytic virus). The release may include, but be not limited to, slow release, sustained release, targeted release, or the like. For example, the vector may include hydrogel capsules, microcapsules, or nanocapsules made of collagen, gelatin, chitosan, alginate, polyvinyl alcohol, polyethylene oxide, starch, cross-linked starch, or the like, or any combination thereof.

In some embodiments, the pharmaceutically acceptable vector may include dispersion media (such as solvents), coatings, buffers, stabilizing formulations, isotonic agents, absorption delaying agents, or the like. Exemplary pharmacologically acceptable vectors may include phosphate-buffered saline, water, emulsions (e.g., oil/water emulsions), various types of wetting agents, sterile solutions, gels, biosorbable matrix materials, other suitable materials, or the like, or any combination thereof.

In some embodiments, the excipient may include, but be not limited to, water, saline, polyethylene glycol, hyaluronic acid, ethanol, and pharmaceutically acceptable salts, for example, salts of inorganic acids (e.g., hydrochloric acids, hydrobromides, phosphates, sulfates, etc.) and salts of organic acids (such as acetates, propionates, benzoates, etc.).

In some embodiments, the cancers that the composition is capable of treating may include, but be not limited to, brain glioma, melanoma, liver cancer, lung cancer, colon cancer, rectal cancer, head and neck tumors, breast cancer, renal cell carcinoma, ovarian cancer, prostate cancer, gastric cancer, lymphoma, pancreatic cancer, bladder cancer, endometrial cancer, cervical cancer, sarcoma (such as soft tissue sarcoma and osteosarcoma), etc.

The composition may be injected into a subject suffering from cancer, e.g., a human or an animal. In some embodiments, the composition may be injected into the subject by one or more modes of administration. The one or more modes of administration may include, but be not limited to, oral administration, injection, or topical administration. Forms of the composition suitable for oral administration may include, but be not limited to, tablets, liposomal formulations, sustained-release capsules, microparticles, microspheres, or any other suitable forms. Forms of the composition suitable for injection may include, but be not limited to, sterile aqueous, oily preparations, or the like. Forms of the composition suitable for topical administration may include, but be not limited to, sterile aqueous or non-aqueous solutions, suspensions, and emulsions. Taking nasal cavity administration as an example, the forms of the composition may include aerosols, mists, powders, solutions, suspensions, gels, or the like.

In some embodiments, the composition may be stored at a suitable temperature, which may include room temperature (about 20° C.), 4° C., −20° C., −80° C., or the like. The composition may also be prepared in various forms convenient for storage and transportation, such as powders. The powder may be a sterile powder and a solvent may be added to the sterile powder and mixed uniformly before use to prepare a solution for oral administration, injection, or topical administration. In some embodiments, the composition may also include components that have antibacterial effects but do not significantly negatively affect the survival of the oncolytic virus, making the composition stable under certain storage conditions (such as refrigeration and freezing) and preventing contamination of microorganisms (such as bacteria and fungi).

In some embodiments, the multiplicity of infection of the oncolytic virus acting on cancer cells in a culture environment may be 0.1, 0.2, 0.5, 0.8, 1.0, 1.5, 2.0, 2.5, etc.

In some embodiments, when the oncolytic virus acts on human non-small cell lung cancer cells at a multiplicity of infection of 2 in a culture environment, it may correspondingly cause at least 30% of the cancer cells to die within 48 hours. In some embodiments, when the oncolytic virus acts on the human non-small cell lung cancer cells at the multiplicity of infection of 2 in a culture environment, it may cause at least 50% of the cancer cells to die within 48 hours. In some embodiments, when the oncolytic virus acts on the human non-small cell lung cancer cells at the multiplicity of infection of 2 in a culture environment, it may correspondingly cause at least 70% of the cancer cells to die within 48 hours.

In some embodiments, when the oncolytic virus acts on human liver cancer cells at the multiplicity of infection of 2 in a culture environment, it may correspondingly cause at least 60% of the cancer cells to die within 48 hours. In some embodiments, when the oncolytic virus acts on the human liver cancer cells at the multiplicity of infection of 2 in a culture environment, it may cause at least 70% of the cancer cells to die within 48 hours. In some embodiments, when the oncolytic virus acts on the human liver cancer cells at the multiplicity of infection of 2 in a culture environment, it may cause at least 80% of the cancer cells to die within 48 hours. In some embodiments, when the oncolytic virus acts on the human liver cancer cells at the multiplicity of infection of 2 in a culture environment, it may cause at least 90% of the cancer cells to die within 48 hours.

In some embodiments, when the oncolytic virus acts on human breast cancer cells at the multiplicity of infection of 2 in a culture environment, it may correspondingly cause at least 30% of the cancer cells to die within 48 hours. In some embodiments, when the oncolytic virus acts on the human breast cancer cells at the multiplicity of infection of 2 in a culture environment, it may cause at least 40% of the cancer cells to die within 48 hours. In some embodiments, when the oncolytic virus acts on the human breast cancer cells at the multiplicity of infection of 2 in a culture environment, it may correspondingly cause at least 60% of the cancer cells to die within 48 hours.

In some embodiments, when the oncolytic virus acts on human pancreatic cancer cells at the multiplicity of infection of 2 in a culture environment, it may correspondingly cause at least 20% of the cancer cells to die within 48 hours. In some embodiments, when the oncolytic virus acts on the human pancreatic cancer cells at the multiplicity of infection of 2 in a culture environment, it may correspondingly cause at least 30% of the cancer cells to die within 48 hours. In some embodiments, when the oncolytic virus acts on the human pancreatic cancer cells at the multiplicity of infection of 2 in a culture environment, it may cause at least 40% of the cancer cells to die within 48 hours.

In some embodiments, when the oncolytic virus acts on the human non-small cell lung cancer cells, human liver cancer cells, human breast cancer cells, or human pancreatic cancer cells at a multiplicity of infection of 0.1 in a culture environment, correspondingly, it may, cause about 50%, 40%, 60%, or 40% of the cancer cells to die within 48 hours.

In some embodiments, when the oncolytic virus acts on the human non-small cell lung cancer cells, human liver cancer cells, human breast cancer cells, or human pancreatic cancer cells at a multiplicity of infection of 1 in a culture environment, correspondingly, it may cause at least 70%, 80%, 60%, or 40% of the cancer cells to die within 48 hours.

In some embodiments, when the oncolytic virus is injected into the subject by injection, the tumor volume may be reduced or even the tumor may be eliminated. For example, when the oncolytic virus is injected into a human non-small cell lung cancer tumor with one injection at a dose of $8 \times 10^6$ pfu or three injections at the dose of $8 \times 10^6$ pfu, it may cause at least 60% or 80% of the tumor volume decreased within 100 days, respectively.

In some embodiments, when the oncolytic virus is injected into the subject by injection, the survival period of the subject may be extended, and/or the survival rate of the subject may be improved. When the oncolytic virus is injected into a subject suffering from colon cancer with three injections at a dose of at least $1 \times 10^6$ pfu, the survival period of the subject may be extended, for example, the survival rate of the subject may reach 90% within 111 days of the injection of the oncolytic virus. In some embodiments, when the oncolytic virus is injected into the subject suffering from colon cancer with three injections at a dose of at least $1 \times 10^7$ pfu, the survival period of the subject may be extended, for example, the survival rate of the subject may reach 40% within 111 days of the injection of the oncolytic virus.

One aspect of the present disclosure may provide an application of the oncolytic virus in preparation of a drug for treating cancer. The oncolytic virus may be used to treat a subject suffering from cancer, e.g., a mammal.

Exemplary cancers may include melanoma, lung cancer, leukemia, gastric cancer, ovarian cancer, pancreatic cancer, breast cancer, prostate cancer, bladder cancer, colon cancer, rectal cancer, liver cancer, cervical cancer, or osteosarcoma. In some embodiments, the cancers may include the lung cancer, liver cancer, breast cancer, or pancreatic cancer.

One aspect of the present disclosure may provide a method for treating cancer. The method may include administering an effective dose of the above-mentioned composition to a subject suffering from cancer. The subject may be a mammal, e.g., a human.

In some embodiments, the effective dose of the composition may be injected into the subject with cancer. For example, the effective dose may be determined based on features of a subject to be treated, an administration route, and/or features (e.g., a type of the cancer, a progression of the cancer, etc.) of the cancer. Specifically, the features of the subject may include, but be not limited to age, gender, height, weight, health status, etc. Therefore, the effective doses described in the embodiments of the present disclosure are exemplary and may be modified by those skilled in the art according to specific situations. For example, ratios of an amount of the oncolytic virus in the composition to a body weight of the subject may range from $0.5 \times 10^6$ pfu/kg-$2.5 \times 10^6$ pfu/kg, $0.70 \times 10^6$ pfu/kg-$2.3 \times 10^6$ pfu/kg, $1 \times 10^6$ pfu/kg-$2 \times 10^6$ pfu/kg, $1.30 \times 10^6$ pfu/kg-$1.70 \times 10^6$ pfu/kg, $1.36 \times 10^6$ pfu/kg-$1.67 \times 10^6$ pfu/kg, $1.40 \times 10^6$ pfu/kg-$1.60 \times 10^6$ pfu/kg, etc.

In some embodiments, the composition may be injected into the subject by a variety of modes of administration. Modes of administration may include, but be not limited to, oral administration, injection, or topical administration. In some embodiments, the composition may be injected into the subject by injection. Exemplary injection manners may include intraperitoneal injection, subcutaneous injection, intramuscular injection, intravenous injection, or the like. In some embodiments, the composition may be injected into a site in or near a tumor of the subject. In some embodiments, the composition may be injected into a tissue or organ of the subject, such as the kidney, liver, heart, thyroid, or joints. In some embodiments, the topical administration may include administering the composition to the skin to alleviate cancers such as skin cancer, lymphoma, or the like. In some embodiments, the topical administration may include vaginal administration, rectal administration, nasal administration, auricular administration, intramedullary administration, intra-articular administration, intra-pleural administration, or the like, or any combination thereof. In some embodiments, the composition may be injected into the subject by a combination of different modes of administration. In some embodiments, the methods may include administering to the subject three times a day, twice a day, once a day, every other day, etc.

The composition of the present disclosure may be used before or after the administration of other pharmaceutical compositions used in the treatment of cancer. Optionally, the composition disclosed in the present disclosure may be combined with other treatment modalities to treat the cancer in the subject. For example, other treatment manners may include, but be not limited to, administering other pharmaceutical compositions that may treat the cancer of the subject, resecting the subject's tumor through surgery, radiotherapy, or the like. Specifically, the pharmaceutical composition that may be used to treat the cancer may include, but be not limited to cytotoxic anticancer drugs and non-cytotoxic anticancer drugs. The non-cytotoxic anticancer drugs may include hormonal drugs (e.g., tamoxifen, exemestane), targeted drugs (e.g., bevacizumab), and immunotherapeutic drugs (e.g., monoclonal antibodies, tumor vaccines), etc.

Experimental methods in the following embodiments are conventional manners unless otherwise specified. Experimental materials used in the following embodiments were purchased from conventional biochemical reagent companies unless otherwise specified.

Embodiment 1: Construction of a Vector of a Recombinant Oncolytic Virus (i.e., an Oncolytic Virus Comprising a Recombinant Nucleic Acid) Strains 1.1 Obtaining a recombinant viral vector R1 by inserting a gene fragment encoding a US11 protein, a BGH Poly A fragment, an EYFP gene fragment, a CMV promoter, a CMV enhancer, and a soluble PD-1 gene fragment into an HSV-1 viral vector.

1.2 Obtaining a linearized viral vector R1 by digesting the constructed viral vector R1 with Hind III and Kpn I.

1.3 Using agarose gel electrophoresis to verify the length of a digested viral vector R1, and recovering the linearized viral vector R1 using a recovery kit.

1.4 Obtaining a recombinant viral vector R2 by inserting a gene fragment encoding CD86 and OKT3 molecules (that is, antibodies to a CD3 molecule) into another HSV-1 viral vector.

1.5 Obtaining the gene fragments encoding the CD86 and OKT3 molecules by digesting a constructed viral vector R2 with Hind III and Kpn I.

1.6 Using the agarose gel electrophoresis to verify the length of the gene fragment encoding the CD86 and OKT3 molecules after digestion, and recovering the gene fragment encoding the CD86 and OKT3 molecules using the recovery kit.

1.7 Obtaining a recombinant viral vector R130 by use a ligase to connect the purified linearized viral vector R1 and the gene fragment encoding the CD86 and OKT3 molecules.

1.8 Using the Hind III and Kpn I to digest the viral vector R130, verifying whether the gene fragment encoding the CD86 and OKT3 molecules have been connected to the linearized viral vector R1, and performing sequencing verification on the viral vector R130.

FIG. 1 is a schematic diagram illustrating a vector plasmid structure of a recombinant oncolytic virus according to some embodiments of the present disclosure. A connection sequence and position of each fragment are shown in FIG. 1.

The wild-type HSV-1 virus and the R130 plasmid were co-transfected into green monkey kidney cells (vero cells), and cell debris was removed after harvesting. A virus suspension obtained after high-speed centrifugation and purification was used as a mixed virus solution and stored at −80° C. for future use. The vero cells were purchased from the American Type Culture Collection (ATCC).

Embodiment 2: Screening Recombinant Oncolytic Virus Strains 2.1 Planting about $4 \times 10^5$ green monkey kidney cells (vero cells) in wells of a 6-well plate.

2.2 After 24 hours, aspirating off a culture medium of the vero cells, rinsing once with 1 ml of preheated serum-free DMEM, and then adding 680 ul of the preheated serum-free DMEM medium.

2.3 Taking out the mixed virus solution from −80° C. and dissolving it in a 4° C. refrigerator.

2.4 Dividing the mixed virus solution into three gradients of 5 ul, 10 ul, and 20 ul, and repeating each gradient twice.

2.5 Inoculating the mixed virus solution of the three gradients into the 6-well plate for culturing the vero cells, shaking back and forth several times, after mixing well, placing the 6-well plate in a 37° C., 5% $CO_2$ cell incubator for 1.5 hours of virus adsorption, and shaking every 15 minutes.

2.6 Preheating water baths at three temperatures of 72° C., 42° C., and 37° C. in advance, dissolving 2% agarose gel (autoclaved) in a 72° C. water bath, preheating a DMEM medium comprising 4% FBS in a 37° C. water bath, and preheating a DMEM medium comprising 1% low-melting point agarose and 2% FBS prepared according to a count of cultured cells in a 42° C. water bath, each 6-well plate needing 2 ml of a DMEM medium comprising 1% agarose gel and 2% FBS.

2.7 Aspirating off the virus-comprising serum-free medium in the 6-well plate, and gently adding 2 ml of the DMEM medium comprising 1% agarose gel and 2% FBS to the wells.

2.8 Sealing the 6-well plate with parafilm and placing it in the refrigerator at 4° C. to allow the low-melting point agarose to solidify, and after 10 minutes, transferring it to a cell culture incubator for normal culture.

2.9 Checking appearance of plaques with green fluorescence every day, when the plaques with green fluorescence are large enough, picking them out using a sterile pipette tip with 200 ul and transferring them into a 0.6 ml sterile centrifuge tube containing 200 ul of serum-free DMEM medium, numbering selected recombinant oncolytic virus strains and storing the recombinant oncolytic virus strains at −80° C. for at least 15 minutes.

2.10 Using the pipette tip to mix the preserved recombinant oncolytic virus strains, re-inoculating them into the vero cells in the 6-well plate according to a certain proportion, and following the above steps for a next round of selection, if all formed plaques containing the green fluorescence, selecting good plaques to amplify and store, and obtaining a selected recombinant oncolytic virus strain.

Embodiment 3, Identification of the Recombinant Oncolytic Virus Strains 3.1 Cultivating a harvested medium and harvested cells after amplification on 10 cm vero cells culture dish, freezing and thawing repeatedly at −80° C. 2-3 times, centrifuging at 3500 rpm at 4° C. for 15 minutes, and taking 200 μl of supernatant.

3.2 Transferring the 200 μl of the supernatant to a 1.5 ml centrifuge tube, adding 400 μl of lysate, and immediately vortexing to mix thoroughly.

3.3 Leaving it at room temperature for 10 minutes, shaking and mixing every 5 minutes.

3.4 Adding 450 μl of absolute ethanol, and immediately vortexing to mix thoroughly.

3.5 Adding the above mixture into an adsorption column, putting the adsorption column into a collection tube, centrifuging at 13000 rpm for 30-60 seconds, and discarding waste liquid in the collection tube.

3.6 Adding 500 μl of a protein-removing solution, centrifuging at 12000 rpm for seconds, and discarding a waste solution.

3.7 Adding 500 μl of a rinsing solution, centrifuging at 12000 rpm for 30 seconds, discarding a waste solution, adding 500 μl of the rinsing solution, and repeating once.

3.8 Putting the adsorption column back into an empty collection tube, centrifuging at 13,000 rpm for 2 minutes, and removing the rinsing solution as much as possible, so as to prevent the residual ethanol in the rinsing solution from inhibiting downstream reactions.

3.9 Taking out the adsorption column, putting it into a centrifuge tube with RNase free, adding 30-50 μl of RNase free water to a middle part of an adsorption membrane, leaving it at the room temperature for 1 minute, and centrifuging at 12000 rpm for 1 minute to obtain genomes of the recombinant oncolytic virus strains.

Figure 2:
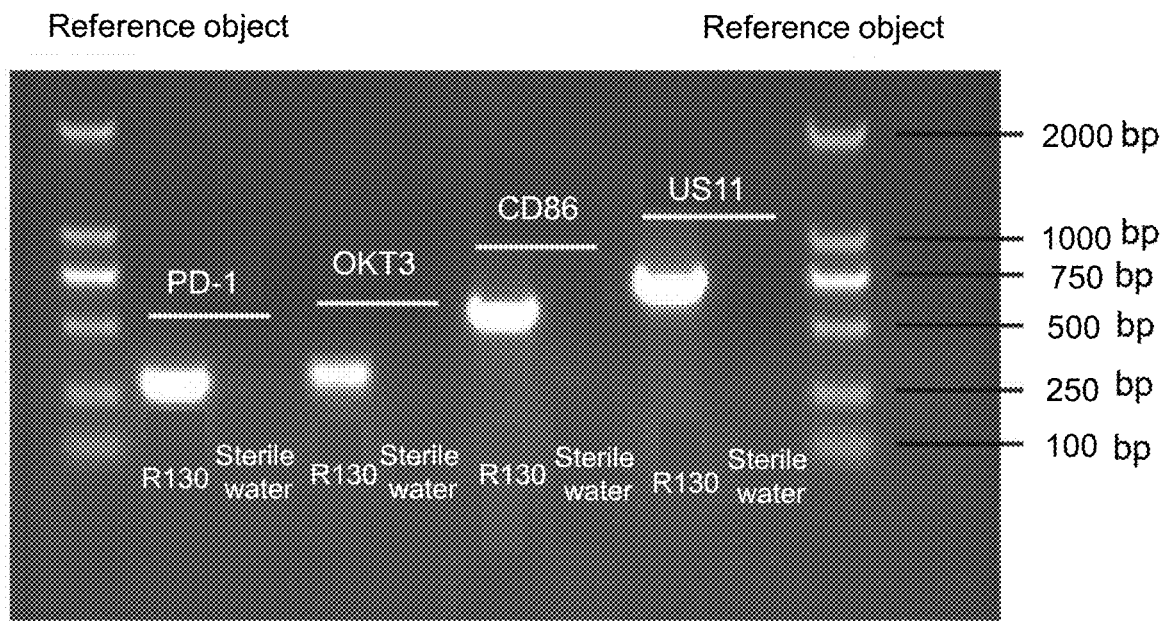
FIG. 2 is an electrophoresis diagram of the verification of each fragment of the recombinant oncolytic virus according to some embodiments of the present disclosure.

3.10 Designing 4 pairs of PCR primers for the inserted ones to amplify the exogenous gene fragments, and verifying 4 amplified exogenous gene fragments by agarose gel electrophoresis. The agarose gel electrophoresis results of PCR-amplified DNA fragments are shown in FIG. 2. As shown in FIG. 2, the single DNA fragment was amplified, and the fragment size was correct, indicating that each exogenous gene fragment has been inserted into the oncolytic virus strain.

3.11 Performing next generation sequencing (NGS) verification on the amplified fragments, performing the sequence comparison by snapgene biological software, and the comparison result was 100%. Thus, it was verified that the PCR-amplified DNA fragment is the target gene sequence without mutation. Therefore, the recombinant HSV-1 virus comprising the recombinant nucleic acid was called HSV1-R130, and it has been deposited in the General Microbiology Center of the China Microbiological Culture Collection Management Committee (CGMCC). The preservation date is May 8, 2021. The registration number of the depository center is CGMCC No. 20319, and the depository address is Institute of Microbiology, Chinese Academy of Sciences, No. 3, No. 1 Courtyard, Beichen West Road, Chaoyang District, Beijing.

Embodiment 4. Recombinant Oncolytic Virus has a Significant Killing Effect on Cancer Cells 4.1 Inoculating human non-small cell lung cancer cells A549, human liver cancer cells HepG2, human breast cancer cells MCF-7, and human pancreatic cancer cells SW1990 in a 12-well plate according to an appropriate inoculation amount for 24 hours. The cells basically covered a monolayer.

4.2 After 24 hours, aspirating off an original culture medium in the 12-well plate, washing it twice with a DPBS or serum-free DMEMP medium, and then adding 300 μl of a serum-free DMEM medium.

4.3 Diluting a stock solution of the recombinant oncolytic virus with 10 times and 100 times.

4.4 According to an initial cell inoculation amount and a virus titer, calculating an amount of added virus per well, and dividing them into following four groups: the multiplicity of infection (MOI) of a control group being 0, an MOI of a low dose group being 0.1; an MOI of a middle dose group being 1.0; and an MOI of a high dose group being 2.0.

4.5 After virus adsorption for 1 hour, replacing with a DMEM maintenance solution containing 2% FBS to continue culturing.

4.6 Processing the cells at 24 hours and 48 hours, respectively, staining the cells with trypan blue, and counting a survival ratio of living cells.

Figure 3:
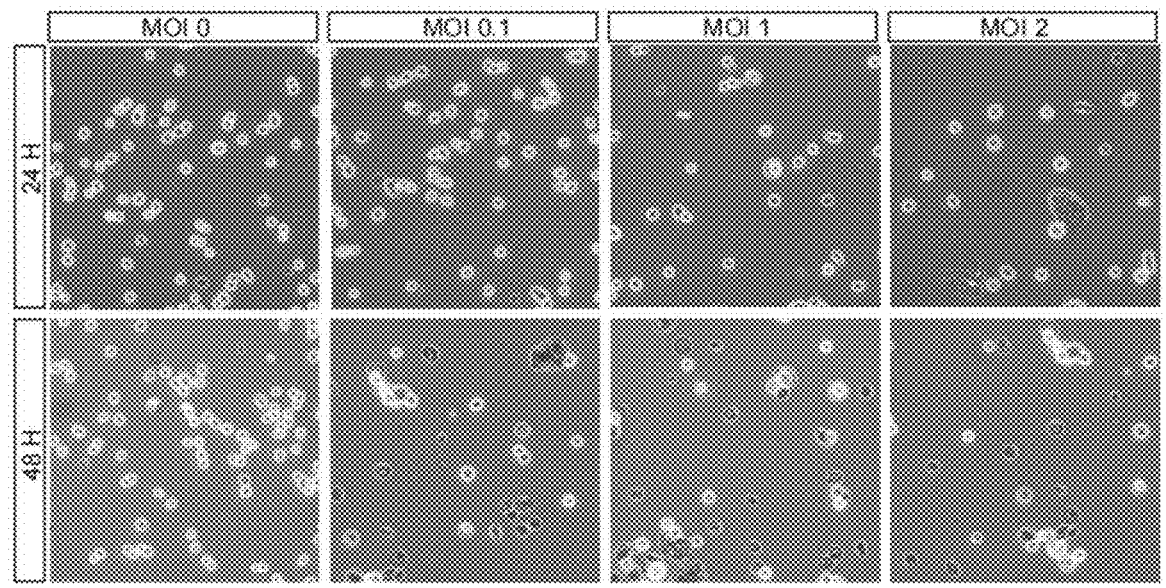
FIG. 3 is a schematic diagram of human non-small cell lung cancer cells A549 transfected by the recombinant oncolytic virus after staining according to some embodiments of the present disclosure.
Figure 4:
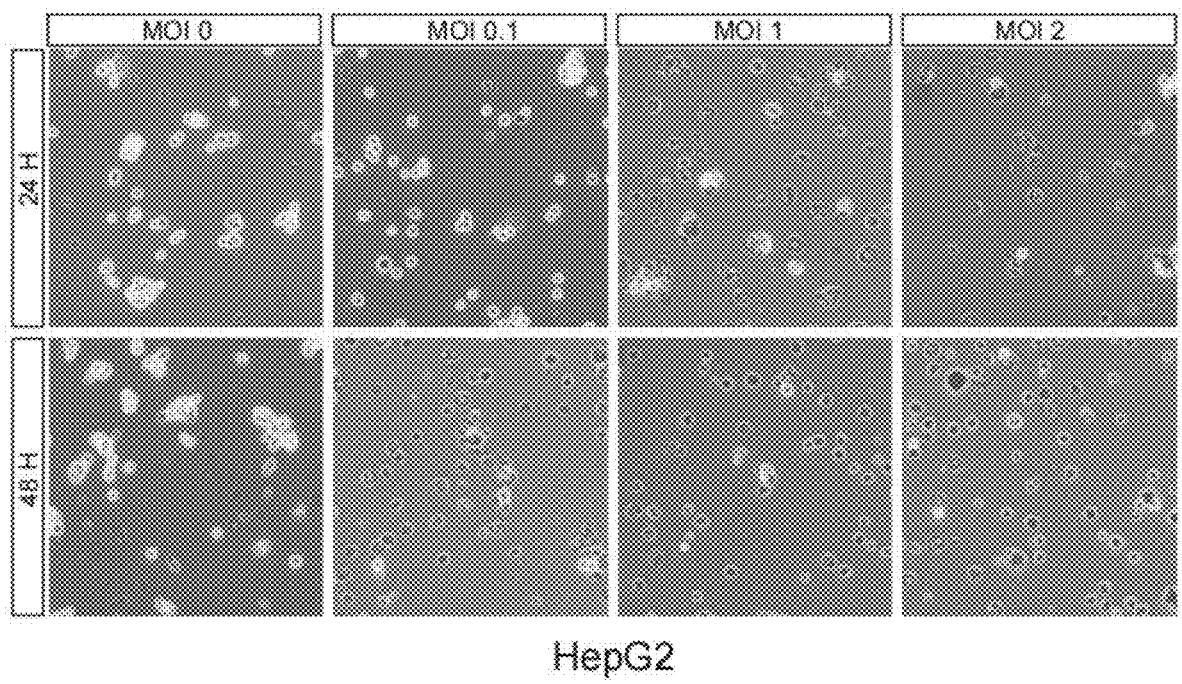
FIG. 4 is a schematic diagram of human liver cancer cells HepG2 transfected by the recombinant oncolytic virus after staining according to some embodiments of the present disclosure.
Figure 5:
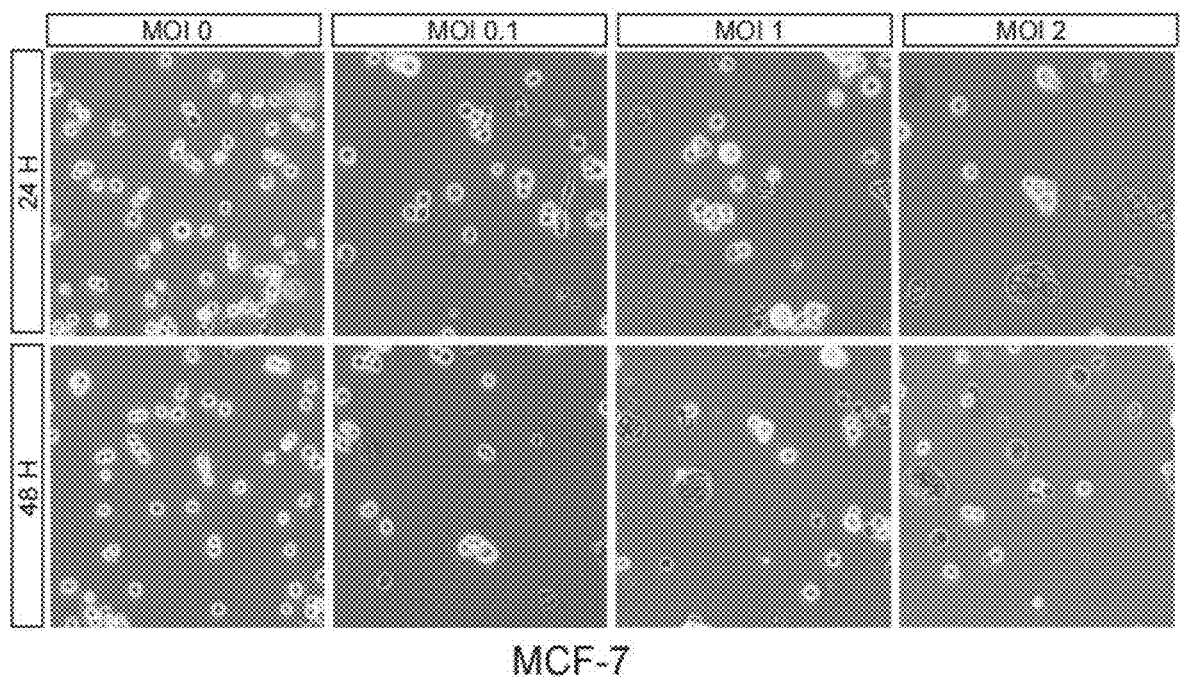
FIG. 5 is a schematic diagram of human breast cancer cells MCF-7 transfected by the recombinant oncolytic virus after staining according to some embodiments of the present disclosure.
Figure 6:
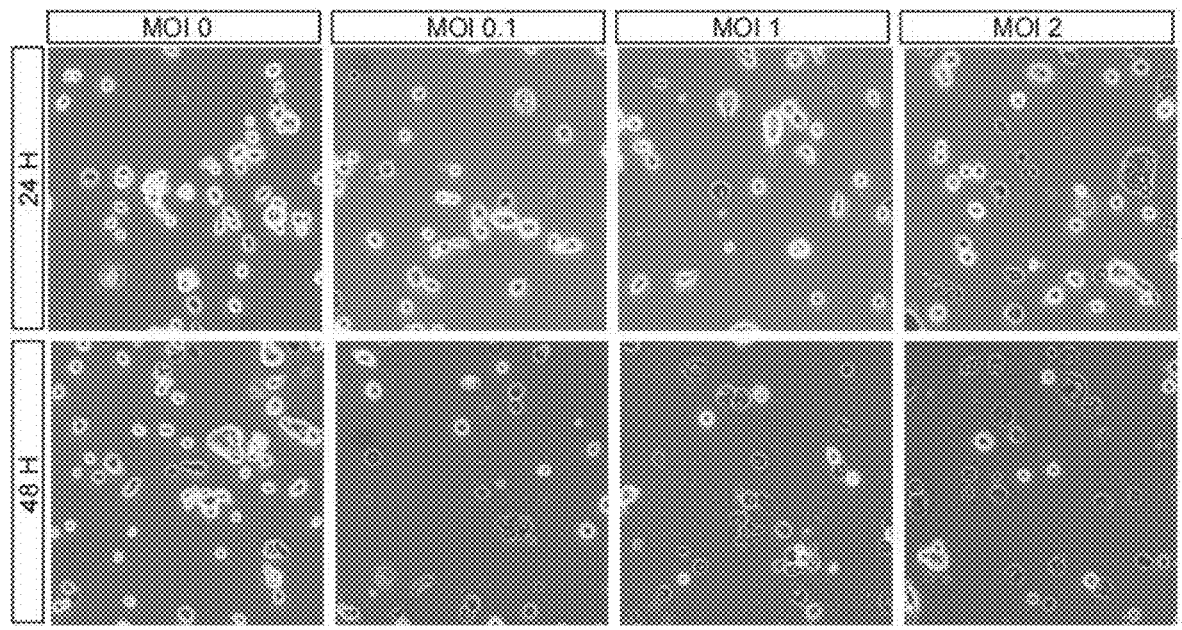
FIG. 6 is a schematic diagram of human pancreatic cancer cells SW1990 transfected by the recombinant oncolytic virus after staining according to some embodiments of the present disclosure.
Figure 7:
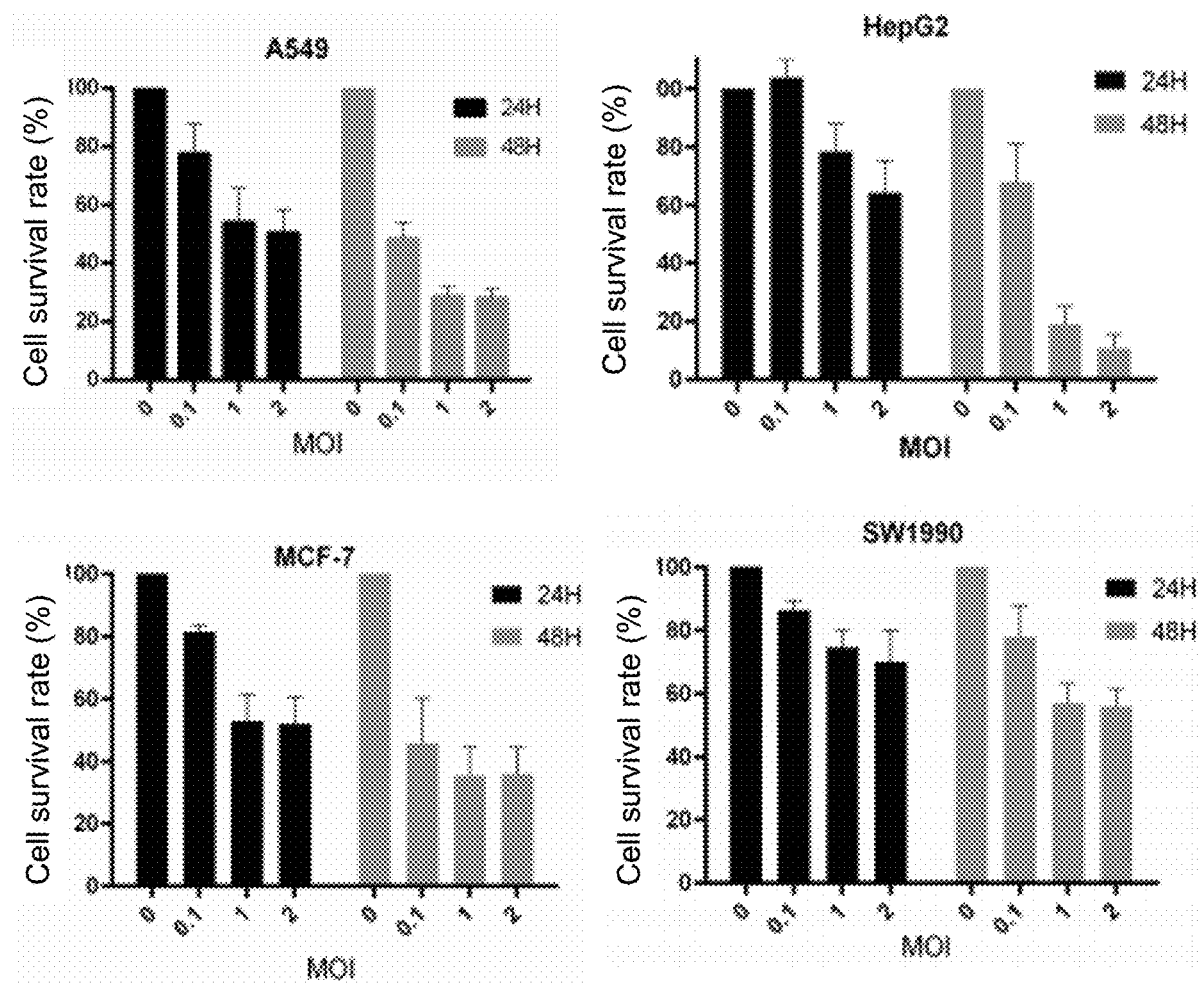
FIG. 7 is a schematic diagram of cell survival rates of the human non-small cell lung cancer cells A549, human liver cancer cells HepG2, human breast cancer cells MCF-7, and human pancreatic cancer cells SW1990 transfected by the recombinant oncolytic virus according to some embodiments of the present disclosure.

FIG. 3 is a schematic diagram of human non-small cell lung cancer cells A549 transfected by the recombinant oncolytic virus after staining according to some embodiments of the present disclosure. FIG. 4 is a schematic diagram of human liver cancer cells HepG2 transfected by the recombinant oncolytic virus after staining according to some embodiments of the present disclosure. FIG. 5 is a schematic diagram of human breast cancer cells MCF-7 transfected by the recombinant oncolytic virus after staining according to some embodiments of the present disclosure. FIG. 6 is a schematic diagram of human pancreatic cancer cells SW1990 transfected by the recombinant oncolytic virus after staining according to some embodiments of the present disclosure. The survival rates (or cell survival rates) of the four stained cancer cells shown in FIGS. 3-6 were calculated, and the results are shown in FIG. 7. FIG. 7 is a schematic diagram of cell survival rates of the human non-small cell lung cancer cells A549, human liver cancer cells HepG2, human breast cancer cells MCF-7, and human pancreatic cancer cells SW1990 transfected by the recombinant oncolytic virus according to some embodiments of the present disclosure.

As shown in FIG. 7, in a control group without adding virus, the four groups of cancer cells A549, HepG2, MCF-7, and SW1990 were cultured for 24 hours and 48 hours, and all the cell survival rates were about 100%. In experimental groups with virus added, low dose (MOI of 0.1), medium dose (MOI of 1), and high dose (MOI of 2) could effectively kill the four cancer cells. The killing effect of virus action time 48 h was significantly higher than that of 24 h action time.

After the cancer cells A549 and MCF-7 were processed with the recombinant oncolytic virus for 24 hours, the cell survival rates in the low, middle, and high dose groups were about 80%, 50%, and 50%. Extending the treatment time to 48 hours, the cell survival rates in the low, middle, and high dose groups were about 50%, 38%, and 38%. Extending the action time of the recombinant oncolytic virus or increasing the dose of recombinant oncolytic virus greatly increased the mortality of the cancer cells A549 and MCF-7, and reduced the survival ability of the cancer cells A549 and MCF-7.

After the cancer cells HepG2 were processed with recombinant oncolytic virus for 24 hours, the cell survival rates in the middle and high dose groups was about 80% and 60%. When the treatment time was extended to 48 hours, the cell survival rate in the low-dose group was 70%, and the cell survival rates in the middle-dose group and high-dose group were only 20% and 10%. It shows that extending the treatment time of the recombinant oncolytic virus or increasing the dose of the recombinant oncolytic virus may greatly increase the mortality of human liver cancer cells HepG2, and reduce the survival ability of the human liver cancer cells HepG2.

After the cancer cells SW1900 were processed with recombinant oncolytic virus for 24 hours, and the cell survival rates in the low, middle and high dose groups were slightly lower than the cell survival rates in the control group. After 48 hours of virus action, the effects were more obvious than those of 24 hours, that is, the cell survival rates were lower. The low, middle, and high dose groups may effectively kill SW1900 cancer cells within 48 hours. The cell survival rate of the low dose group was less than 80%. There was little difference between the middle and high dose groups, and the cell survival rates were less than 60%. The above results indicate that the recombinant oncolytic virus may quickly kill the cancer cells SW1900 in a short time period (for example, 48 hours), and the higher the dose of the recombinant oncolytic virus, the lower the cell survival rate of the cancer cells.

Therefore, the recombinant oncolytic virus may quickly and effectively kill the four cancer cells, A549, HepG2, MCF-7, and SW1990, and had obvious inhibitory effects on lung cancer, liver cancer, breast cancer, and pancreatic cancer. The inhibitory effect on the liver cancer was the most effective. Extending the virus action time or increasing the virus dose greatly reduced the cell viability of the cancer cells.

Embodiment 5. The Recombinant Oncolytic Virus has an Obvious Curative Effect on Immunodeficiency Nude Mice Suffering from Non-Small Cell Lung Cancer In order to test the efficacy of R130, non-small cell lung cancer cells A549 were intraperitoneally injected into immunocompetent mice to construct a non-small cell lung cancer mouse model. In peritoneal cavities of the mice suffering from the non-small cell lung cancer, an R130 virus solution was injected. The experiment was divided into three groups, namely a control group CK, which was directly injected with 100 µL of PBS (pH7.4) buffer; a high-dose group, which was injected with a dose of $8\times10^6$ pfu every three days for three consecutive injections; and a low-dose group, which was injected with a dose of $8\times10^6$ pfu once. Body conditions of the mice were observed daily, and the body weights of the mice were monitored every two days. Tumor diameters were monitored using a vernier caliper and tumor volumes were calculated, and the mice were euthanized when they survived treatment for 111 days.

Figure 8:
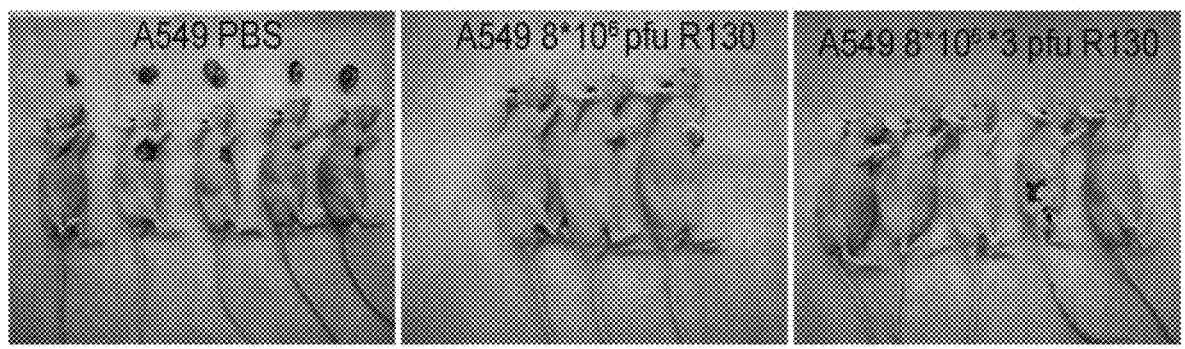
FIG. 8 is a schematic diagram of a lung cancer mouse model constructed by treating immunodeficient nude mice with the recombinant oncolytic virus according to some embodiments of the present disclosure.

FIG. 8 is a schematic diagram of a lung cancer mouse model constructed by treating immunodeficient nude mice with the recombinant oncolytic virus according to some embodiments of the present disclosure. As shown in FIG. 8, when the oncolytic virus was injected into non-small cell lung cancer tumors with one injection of a dose of $8\times10^6$ pfu or three injections of the dose of $8\times10^6$ pfu, it caused at least 60% or 80% reduction in a tumor volume.

Embodiment 6. Recombinant Oncolytic Virus has a Significant Curative Effect on Immune Intact Mice Suffering from Colon Cancer In order to test the efficacy of R130, a CT26 colon cancer mouse model was established by intraperitoneally injecting the colon cancer cells CT26 into the immune intact mice. In peritoneal cavities of the immune intact mice suffering from the colon cancer, an R130 virus solution was injected. The test was divided into a control group CK, which was directly injected with 100 µL PBS (pH7.4) buffer, a high-dose group, which was injected with a dose of $1\times10^7$ pfu every three days for three consecutive injections; and a low-dose group, which was injected with a dose of $1\times10^6$ pfu every three days for three consecutive injections.

Figure 9:
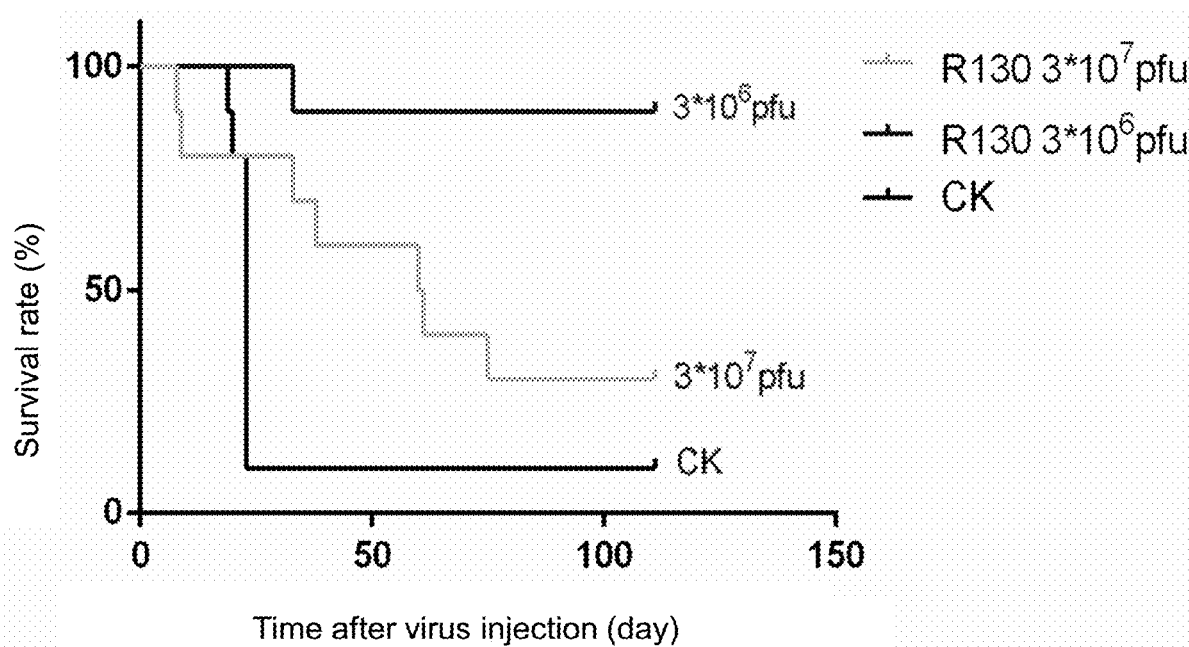
FIG. 9 is a schematic diagram of a time and a mouse survival rate of a CT26 celiac colon cancer mouse model treated with different doses of the recombinant oncolytic virus according to some embodiments of the present disclosure.

FIG. 9 is a schematic diagram of a time and a mouse survival rate of a CT26 celiac colon cancer mouse model treated with different doses of the recombinant oncolytic virus according to some embodiments of the present disclosure. As shown in FIG. 9, in a control group injected with PBS, after 33 days of injection, the survival rate of mice was 10%, and 90% of the mice died, while survival rates of mice injected with virus amounts of $3\times10^7$ pfu and $3\times10^6$ pfu in the experimental groups were 100% and 80%, respectively. At the end of the 111-day experiment, mice in the experimental groups with the virus amounts of $3\times10^7$ pfu and $3\times10^6$ pfu still had a relatively high survival rate, that is, 90% and 40%, respectively.

Therefore, the recombinant oncolytic virus significantly improved the viability of tumor-bearing mice. After injecting the virus with a dose of $10^7$ pfu for 3 times, 90% of mice with abdominal tumors could survive for a long time.

The recombinant oncolytic virus and an application thereof disclosed in the present disclosure may bring beneficial effects including, but not limited to: (1) the nucleic acid fragment encoding the soluble PD-1 molecule in the recombinant oncolytic virus may relieve or reduce the inhibitory effect of the T cells on the oncolytic virus, thereby enhancing the survival and proliferation of the oncolytic virus in cells of the host; (2) the nucleic acid fragment encoding the antibody of the CD3 molecule in the recombinant oncolytic virus may activate the proliferation and activation of the T cells and enhance the anti-tumor effect of the immune system; (3) the nucleic acid fragment encoding the CD86 molecule in the recombinant oncolytic virus may further activate the T cells and enable the T cells to proliferate and differentiate; and (4) the nucleic acid fragment encoding the US11 protein in the recombinant oncolytic virus may enhance the ability of the oncolytic virus to evade the host's natural immune defense, extending a residence time of the oncolytic virus in the body, thereby enhancing the targeted infection and killing effect of cancer cells.

It should be noted that different embodiments may have different beneficial effects. In different embodiments, the possible beneficial effects may be any one or a combination of the above, or any other possible beneficial effects.

It should be understood by those skilled in the art that the above embodiments are only for illustrating the present disclosure, and do not limit the present disclosure. Any modifications, equivalent replacements, and changes made within the spirit and principles of the present disclosure shall be included within the protection scope of the present disclosure.

What is claimed is:

1. An oncolytic virus containing a recombinant nucleic acid, wherein the recombinant nucleic acid comprises:
   (i) a first nucleic acid fragment encoding a soluble PD-1 molecule;
   (ii) a second nucleic acid fragment encoding a CD86 molecule;
   (iii) a third nucleic acid fragment encoding an antibody to a CD3 molecule; and
   (iv) a fourth nucleic acid fragment encoding a US11 protein, wherein:
      the oncolytic virus is an HSV-1 virus, and
      the recombinant nucleic acid has a sequence of SEQ ID NO: 5.

2. A composition for treating cancers, wherein the composition comprises the oncolytic virus according to claim 1 and a pharmacologically acceptable vector or excipient; and wherein the cancers are non-small cell lung cancers, liver cancers, breast cancers, pancreatic cancers, or colon cancers.

3. The composition of claim 2, wherein the composition is used for treating the non-small cell lung cancers or the colon cancers.

4. A method for treating cancers, comprising: administering the composition of claim 2 to a subject suffering from any of the cancers, wherein
   the cancers are non-small cell lung cancers, liver cancers, breast cancers, pancreatic cancers, or colon cancers.

5. The method of claim 4, wherein the cancers are the non-small cell lung cancers or the colon cancers.

6. The method of claim 4, wherein a ratio of an amount of the oncolytic virus in the composition to a body weight of the subject is in a range of $1\times10^6$ pfu/kg-$2\times10^3$ pfu/kg.

7. The method of claim 4, wherein a ratio of an amount of the oncolytic virus in the composition to a body weight of the subject is in a range of $1.30\times10^6$ pfu/kg-$1.70\times10^3$ pfu/kg.

8. The method of claim 4, wherein the administering the composition to a subject suffering from cancers includes:
   administering the composition to the subject by injection.

9. The method of claim 8, wherein the administering the composition to the subject by injection includes:
   injecting the composition into the subject at a site in or near a tumor.

* * * * *

SEQUENCE LISTING

```
Sequence total quantity: 5
SEQ ID NO: 1           moltype = DNA  length = 718
FEATURE                Location/Qualifiers
source                 1..718
                       mol_type = other DNA
                       organism = synthetic construct
SEQUENCE: 1
ttaagataca ttgatgagtt tggacaaacc acaactagaa tgcagtgaaa aaaatgcttt   60
atttgtgaaa tttgtgatgc tattgcttta tttgtaacca ttataagctg caataaacaa  120
gtttcaggtt tggaactggc cggctggcct gggtgagggg ctggggtggg ctgtgggcac  180
ttctgccctt ctctctgtca ccctcagttc tgcccgcagg ctctctttga tctgcgcctt  240
gggggccagg gagatggccc cacagaggta ggtgccgctg tcattgcgcc gggccctgac  300
cacgctcatg tggaagtcac gcccgttggg cagttgtgtg acacggaagc ggcagtcctg  360
gccgggctgg ctgcggtcct cggggaaggc ggccagcttg tccgtctggt tgctggggct  420
cattctatac cagtttagca cgaagctctc cgatgtgttg gagaagctac aggtgaaggt  480
ggcgttgtcc ccttcggtca ccacgagcag ggctgggag aaggtggggg ggttccaggg  540
cctgtctggg gagtctaaga accatcctgg ccgccagccc agttgtagca ccgcccgac  600
gactggccag ggcgcctgtg ggatctgcat ctggagctag cgtctgaaac gagacgctaa  660
ttagtgtata tttttcaat tttaccggat atttatattc caaaaaaaaa aaataaaa     718

SEQ ID NO: 2           moltype = DNA  length = 1432
FEATURE                Location/Qualifiers
source                 1..1432
```

```
                        mol_type = other DNA
                        organism = synthetic construct
SEQUENCE: 2
cagagtgcca gccctgggac cgaaccccgc gtttatgaac aaacgaccca acacccgtgc    60
gttttattct gtcttttat tgccgtcata gcgcgggttc cttccggtat tgtctccttc    120
cgtgtttcag ttagcctccc ccgtttaaac tcattactaa ccggtaggga tcgaacccctt  180
ttaaaaacat gtatcacttt tgtcgcatga agatgtcttc gaacttttaa aaacacgctg   240
ggcttcatca gatctttcag gtatatggat tttttctctt tcttggtct gttcactctc    300
ttccctctcc attgtgttgg ttccacattt ataagagttg cgaggccgct tcttcttctt   360
ccatttccat agaattagac agaaaaccat cacacatata ataactgttg gaagtacagc   420
tgtaatccaa ggaatgtggt ctgggggagg ctgagggtcc tcaagctcta tagagaaagg   480
tgaagataaa agccgcgtct tgtcagtttc cagaatacag aagatggtca tattgctcgt   540
aacatcaggg aatgaaacag acaagctgat ggaaacgtcg tacagttctg tgacattatc   600
ttgagatttc tgcataatac catcatactc gatagttgaa ttcttgttc ttagcaaaac   660
actcatcttc ttaggttctg ggtaaccgtg tatagatgaa caggtcaaat ttatgtacac    720
atttctgtt atattagaaa ttggtactat ttcaggttga ctgaagttag caagcactga    780
cagttcagag ttcatctggt ggatgcgaat cattcctgtg ggcttttgt gatggatgat    840
acattgatac aagcccttgt ccttgatctg aagattgtga agtctcaggg tccaactgtc   900
cgaatcaaaa cttgtgcggc ccatatactt ggaatgaaca ctgtcaaatt tctctttgcc   960
taagtatacc tcattcagaa ccaagttttc ctggtcctgc caaaatacta ctagctcact  1020
caggctttgg ttttgagagt ttgcaaattg gcatggcagg tctgcagtct cattgaaata  1080
agcctgaatc ttcagaggag cagcaccaga gagcaggaag gccatcacaa agagaatgtt  1140
actcagtccc atagtgcact ggggatccat ggtgcacacc aatgtggtga atggtcaaat  1200
ggcgtttatt gtatcgagct aggcacttaa atacaatatc tctgcaatgc gcaattcagt  1260
ggttcgtcca atccatgtca gacccgtctg ttgccttcct aataaggcac gatcgtacca  1320
ccttacttcc accaatcggc atgcacgtgt ctttttctct ccttgtaagg catgttgcta  1380
actcatcgtt accatgttgc aagactacaa gagtattgca taagactaca tt           1432

SEQ ID NO: 3           moltype = DNA  length = 2095
FEATURE                Location/Qualifiers
source                 1..2095
                       mol_type = other DNA
                       organism = synthetic construct
SEQUENCE: 3
gggggctat aaaagggggt ggggcgttc gatgcggctc tgcatcccgc aggtgctgtt      60
ggccttgttc ctttccatgc tgacagggcc gggagaaggc agctacccctt acgatgtacc   120
tgattacgcc caagtgcagc ttcagcagag cggcgctgag ctggcccggc ccggggcctc   180
tgtgaaaatg agctgcaagg cttccggtta caccttaca aggtacacaa tgcactgggt    240
gaagcaggc ccagggcagg gctagagtg gatcggctac ataaacccat ctcgggata    300
tacaaactac aatcaaaagt tcaaagacaa ggccacactg acaacggaca agtcaagcag   360
cacagcttac atgcaactgt catctctgac atccgaggat agcgccgttt actattgcgc   420
cagatactat gatgaccact attgcttgga ctactgggga cagggaacaa ccctcacagt   480
tagctccggc ggggggggca gtggaggtgg aggatctggg ggcggcggta gtcagatcgt   540
cctcacacag tctccggcca taatgtccgc ctccccgga gagaaggtta ctatgacatg    600
ttccgcatct tcctctgtgt catatatgaa ttggtatcag cagaagagtg gcacctctcc   660
taaacgctgg atttacgata cctctaaact ggcgtccggg gtgcctgcac atttcagagg   720
atcaggctcc ggtacgagtt attcactcac aatatctgta atggaggccg aagatgccgc   780
tacttactac tgccaacaat ggtcaagcaa ccccttcact tcggagcg ggacaaagct    840
ggagatcaac atggcctcct ctgggtatgt cctccaggcg gaactctccc cctcaactga   900
gaactcaagt caactggact tcgaagatgt atggaactct tcctatggtg tgaatgattc   960
cttcccagat ggagactatg atgccaacct ggaagcagcc gcccctgcc actcctgtaa   1020
cctgctggat gactctgcac tgccctttct catcctcacc agtgtcctgg gtatcctagc   1080
tagcagcact gtcctcttca tgcttttcag acctctcttc cgctggcagc tctgccctgg  1140
ctggcctgtc ctggcacaac tggctgtggg cagtgccctc ttcagcattg tggtgcccgt  1200
cttggcccca gggctaggta gcactcgcag ctctgccctg tgtagcctgg gctactgtgt  1260
ctggtatggc tcagcctttg cccaggcttt gctgctaggg tgccatgcct ccctgggcca  1320
cagactgggt gcaggccagg tccccaggcct caccctgggg ctcactgtgg gaatttgggg  1380
agtggctgcc ctactgacac tgcctgtcac cctggccagt ggtgcttctg gtggactctg  1440
caccctgata tacagcacgg agctgaaggc tttgcaggcc acacacactg tagcctgtct  1500
tgccatcttt gtcttgttgc cattgggtt gtttggagcc aagggctgaa agaaggcatt  1560
gggtatgggg ccaggcccct ggatgaatat cctgtgggcc tggtttattt tctggtggcc  1620
tcatggggtg gttctaggac tggatttcct ggtgaggtcc aagctgttgc tgttgtcaac  1680
atgtctggcc cagcaggctc tggacctgct gctgaacctg gcagaagccc tggcaatttt  1740
gcactgtgtg gctacgcccc tgctcctcgc ctattctgc caccaggcca cccgcacccct  1800
cttgccctct ctgcccctcc ctgaaggatg gtcttctcat ctggacaccc ttggaagcaa  1860
atcctaacga ctgtgccttc tagttgccag ccatctgttg tttgcccctc cccgtgcct   1920
tccttgaccc tggaaggtgc cactcccact gtccttttcct aataaaatga ggaaattgca  1980
tcgcattgtc tgagtaggtg tcattctatt ctgggggtg gggtggggca ggacagcaag   2040
ggggaggatt gggaagacaa tagcaggaat gctgggggtg cggtgggctc tatgg         2095

SEQ ID NO: 4           moltype = DNA  length = 1247
FEATURE                Location/Qualifiers
source                 1..1247
                       mol_type = other DNA
                       organism = synthetic construct
SEQUENCE: 4
ttctagagtc acgacgcatt tgcccccgtc cccgcagcaa cacacaaagc gatttcaatt    60
ttcacgattt tattattaat tacaccaacc ccctgtcccc cggacgtgg tcaggaccgg   120
ggtccgcac ccaaacgcac gaaacaaatg ctggcagtgt gccgaatata accccgcgta    180
```

```
ggaacacgtc gacgcgtgcg ccaaacagca ccagaaggcg catgccatca gcaggtcgtg    240
catatggcga tgtgtttgga cgcagggcgc agccgcggcg ataaaattca tggcggccgt    300
ccgccaggge cacagcggcg aggactccct gttggcccga agccattggg tatgaaccag    360
ctgcgcctcc tgtccgaccc tggctcccgc cagcgggggc ggtgggtcgt gggtgttgag    420
agcacacagg cgggacacct cgatcaccgt ccgaaaaaag gcccggtggc ccgcgggcag    480
catctgcagg tgcgccaggg cctgggcgtt gagagggtac aactcggagc cgggggactc    540
cggggggccgg tccgcgcggt gccgcgagtt ggcacgcttt ggggcccggg tgtcggacgc    600
gggcgcgtta tggatcccga cgcggggcag aacgtacgtg cgttggcgcg gcgatgaggg    660
gtccgggctg ccgaggggg  cgtagggac  cgggctaggc aagcccgcgg gttgcgcggg    720
gttcccgtgg gggtctaggc tccctgggca cccgtgggca tcgtggggt  cgcgggtccc    780
tgggtatgcg cgggaccctg ggttctctgg gagatcgtgg aactcgccgt tccctgggct    840
ctcgggaac  ccggggctcc ctggggacac gtggtgccct gggaattctt gatggtcgga    900
cggcttcaga tggcttcggg atcgagaggg ccgcacagac tcgtagtaga cccgaatctc    960
cacgtttccc cgccgccgga tcatggtcgc cgccccggtc gccgggccg  tcggtcggaa   1020
gcgagtgccc ttcaagcgtg tccgctcctc tgggctgcat gccgtcggat ggggtgcctt   1080
ttaaggaaag gtctcggctg cccgcccaa  ccggggtttg ggggtgggcc ggggaaaccc   1140
cggatgccat ggcattcgtt tattacaaga attaaatcaa gttggtatag tcttaaaact   1200
gcttgatcat gatcaacgta ataatcgccg tggatgtcca ttggtct                 1247

SEQ ID NO: 5       moltype = DNA   length = 8734
FEATURE            Location/Qualifiers
source             1..8734
                   mol_type = other DNA
                   organism = synthetic construct
SEQUENCE: 5
ggaggaaggg agggaggagg gtactggggg tgaagaaggg ggggggaga  agcgagaaca     60
ggaaaggcga tggagcccgg cagaacaccg aggaaaaaaa aaccacacgc catgcgccgg    120
gccgttgtgg ggccccgggc cggggcccct tgggtccgcc ggggcccggg gccgggccgc    180
cacggggggcc ggccgttggc ggtaacccgg agtgttcatc tcaggccccg ggccgggaac   240
ccggaaaaagc ctcggggggg ccttttttcgc gtccgcgtgg ggcgagcggg tccggacggg   300
gcccggaccg ccgcggtcgg gggccctcg  tccgggccg  tacgcggcct tcgccccgtg    360
aggggacaga cgaacgaaac attccggcga cggaacgaaa aacaccccag acgggttaaa    420
gaaacagaaa ccgcaacccc caccacccccc gaaacgggga aaacgaaaaa acagaccagc    480
ggccggccgg cgcttagggg gaggatgtcg ccgacgcccc ttggccgccc cggctgcagg    540
ggggccggga gagccgcggc acccgacgc  gcccggaaag tctttcgcac cacccgcgat    600
cggcacggcc gcgcccccgc ttttataaag gctgagatga cgcagcaaaa acaggccaca    660
gcaccacgtg ggtaggtgat gtaattttat tttcctcgtc tgcggcctaa tggatttccg    720
ggcgcggtgc ccctgtctgc agagcactta acggaattct agagtcacga cgcatttgcc    780
cccgtccccg cagcaacaca caaagcgatt tcaattttca cgattttatt attaattaca    840
ccaaccaccc tgtccccggg acgtggtcag gaccgggggt ccgcacccaa acgcacgaaa    900
caaatgctgg cagtgtgccg aatataaccc cgcgtaggaa cacgtcgacg cgtgcgccaa    960
acagcaccag aaggcgcatg ccatcagcag gtcgtgcata tggcgatgtg tttgacgca    1020
gggcgcagcc gcggcgataa aattcatggc ggccgtccgc cagggccaca gcggcgagga   1080
ctccctgttg gcccgaagcc attgggtatg aaccagctgc gcctcctgtc cgaccctggc   1140
tcccgccagc gggggcggtg ggtcgtgggt gttgagagca cacaggcggg acacctcgat   1200
caccgtccga aaaaaggccc ggtggccgc  gggcagcatc tgcaggtgcg ccagggcctg   1260
ggcgttgaga gggtacaact cggagccggg ggactccggg ggccggtgcc   1320
cgagttggca cgctttgggg cccggtgtc  ggacgcgggc gcgttatgga tcccgacgcg   1380
gggcagaacg tacgtgcgtt ggcgcggcga tgaggggtcc gggctgccga ggggggcgta   1440
ggggaccggg ctaggcaagc ccgcgggttg cgcggggttc ccgtggggt  ctaggctccc   1500
tggggcaccg tggggtcgt  ggggtcgcg  ggtcctagg  tatgcgggg  accctgggtt   1560
ctctgggaga tcgtggaact cgcggttccc tgggctctcg gggaaccgg  ggctccctgg   1620
ggacacgtgg tgccctggga attcttgatg gtcggacggc ttcagatggc ttcgggatcg   1680
agagggccgc acagactcgt agtagacccg aatctccacg tttccccgcc gccggatcat   1740
ggtcgccgcc ccggtgcggg ggcccgtcgg tcggaagcga gtgcccttca agcgtgtcgc   1800
ctcctctggg ctgcatgccg tcgatgggg  tgccttttaa ggaaaggtct cggctgcccg   1860
ccccaaccgg ggtttggggg tgggccgggg aaacccccgga tgccatggca ttcgtttatt   1920
acaagaatta aatcaagttg gtatagtctt aaaactgctt gatcatgatc aacgtaataa   1980
tcgccgtgga tgtccattgg tctaattccc atagagccca ccgcatccca agcattcctg   2040
ctattgtctt cccaatcctc ccccttgctg tcctgcccca ccccaccccc cagaatagaa   2100
tgacacctac tcagacaatg cgatgcaatt tcctcatttt attaggaaag gacagtggga   2160
gtggcacctt ccagggtcaa ggaaggcacg ggggaggggc aaacaacaga tggctggcaa   2220
ctagaaggca cagtcgttac ttgtacagct cgtccatgcc gagagtgatc ccggcggcgg   2280
tcacgaactc cagcaggacc atgtgatcgc gcttctcgtt ggggtctttg ctcaggcgcg   2340
actggtagct caggtagtgg ttgtcgggca gcagcacggg gccgtcgccg atgggggtgt   2400
tctgctggta gtggtcggcg agctgcacgc tgccgtcctc gatgttgtgg cggatcttga   2460
agttcacctt gatgccgttc ttctgcttgt cggccatgat atagacgttg tggctgttgt   2520
agttgtactc cagcttgtgc cccaggatgt tgccgtcctc cttgaagtcg atgcccttca   2580
gctcgatgcg gttcaccagg gtgtcgccct cgaacttcac ctcggcgcgg gtcttgtagt   2640
tgccgtcgtc cttgaagaag atggtgcgct cctggacgta gccttcggc  atggcggact   2700
tgaagaagtc gtgctgcttc atgtggtcgg ggtagcgggc gaagcacttc aggccgtagc   2760
cgaaggtggt cacgagggtg gccaggggca cgggcagctt gccggtggtg cagatgaact   2820
tcagggtcag cttgccgtag gtggcatcgc cctcgccctc gccggacacg ctgaacttgt   2880
ggccgtttac gtcgccgtcc agctcgacca ggatgggcac cacccggtg  aacagctcct   2940
cgcccttgct caccatctca ccatggtggc gtcggtagc  gctagcgat  ctgacggttc   3000
actaaaccag ctctgcttat atagacctcc caccgtacac gcctaccgcc catttgcgtc   3060
aatgggcggg agttgttacg acattttgga aagtccgtt  gatttggtg  ccaaaacaaa   3120
ctcccattga cgtcaatggg gtggagactt ggaaatcccc gtgagtcaaa ccgctatcca   3180
cgcccattga tgtactgcca aaaccgcatc accatggtaa tagcgatgac taatacgtag   3240
```

```
atgtactgcc aagtaggaaa gtcccataag gtcatgtact gggcataatg ccaggcgggc   3300
catttaccgt cattgacgtc aatagggggc gtacttggca tatgatacac ttgatgtact   3360
gccaagtggg cagtttaccg taaatactcc acccattgac gtcaatggaa agtccctatt   3420
ggcgttacta tgggaacata cgtcattatt gacgtcaatg ggcggggtc gttgggcggt    3480
cagccaggcg ggccatttac cgtaagttat gtaacgcgga actccatata tgggctatga   3540
actaatgacc ccgtaattga ttactattaa taactaatgc atggcggtaa tacggttatc   3600
cacgcggccg cctagcttgc atgcaggcct ctgcagtcga cgggcccggg atccgattaa   3660
gatacattga tgagtttgga caaaccacaa ctagaatgca gtgaaaaaaa tgctttattt   3720
gtgaaatttg tgatgctatt gctttatttg taaccattat aagctgcaat aaacaagtt    3780
caggtttgga actggccggc tggcctgggt gaggggctgg ggtgggctgt gggcacttct   3840
gcccttctct ctgtcaccct cagttctgcc cgcaggctct ctttgatctg cgccttgggg   3900
gccagggaga tggcccacca gaggtaggtg ccgctgtcat tgcgccgggc cctgaccacg   3960
ctcatgtgga agtcacgccc gttgggcagt tgtgtgacac ggaagcggca gtcctggccg   4020
ggctggctgc ggtcctcggg gaaggcggcc agcttgtccg tctggttgct ggggctcatt   4080
ctataccagt ttagcacgaa gctctccgat gtgttggaga agctacaggt gaaggtggcg   4140
ttgtccccct cggtcaccac gagcagggct ggggagaagg tgggggggtt ccagggcctg   4200
tctggggagt ctaagaacca tcctggccgc cagcccagtt gtagcaccgc ccagacgact   4260
ggccagggcg cctgtgggat ctgcatctgg agctagcgtc tgaaacgaga cgctaattag   4320
tgtatatttt ttcaattta ccggatattt atattccaaa aaaaaaaaat aaaaatctag    4380
atgcattcgc gaggtaccca gagtgccagc cctgggaccg aaccccgcgt ttatgaacaa   4440
acgacccaac acccgtgcgt tttattctgt cttttattg ccgtcatagc gcgggttcct    4500
tccggtattg tctccttccg tgtttcagtt agcctcccc gtttaaactc attactaacc    4560
ggtagggatc gaacccttt aaaaacatgt atcacttttg tcgcatgaag atgtcttcga    4620
acttttaaaa acacgctggg cttcatcaga tctttcaggt atatggattt tttctctttt   4680
cttggtctgt tcactctctt ccctctccat tgtgttggtt ccacatttat aagagttgcg   4740
aggccgcttc ttcttcttcc attttcatag aattagacag aaaaccatca cacatataat   4800
aactgttgga agtacagctg taatccaagg aatgtggtct gggggaggct gagggtcctc   4860
aagctctata gagaaaggtg aagataaaag ccgcgtcttg tcagtttcca gaatacagaa   4920
gatggtcata ttgctcgtaa catcagggaa tgaaacagac aagctgatgg aaacgtcgta   4980
cagttctgtg acattatctt gagatttctg cataatacca tcatactcga tagttgagtt   5040
cttggttctt agcaaaacac tcatcttctt aggttctggg taaccgtgta tagatgagca   5100
ggtcaaattt atgtacacat tttcgtttat attagaaatt ggtactatt  caggttgact   5160
gaagttagca agcactgaca gttcagagtt catctggtgg atgcgaatca ttcctgtggg   5220
cttttttgtga tggatgatac attgatacaa gcccttgtcc ttgatctgaa gattgtgaag   5280
tctcagggtc caactgtccg aatcaaaact tgtgcgccc atatacttgg aatgaacact    5340
gtcaaatttc tctttgccta agtataccte attcagaacc aagttttcct ggtcctgcca   5400
aaatactact agctcactca ggctttggtt ttgagagttt gcaaattggc atggcaggtc   5460
tgcagtctca ttgaaataag cctgaatctt cagaggagca gcaccagaga gcaggaaggc   5520
catcacaaag agaatgttac tcagtcccat agtgcactgg ggatccatgg tgcacaccaa   5580
tgtggtgaat ggtcaaatgg cgtttattgt atcgagctag gcacttaaat acaatatctc   5640
tgcaatgcgc aattcagtgg ttcgtccaat ccatgtcaga cccgtctgtt gccttcctaa   5700
taaggcacga tcgtaccacc ttacttcac caatcggcat gcacggtgct ttttctctcc    5760
ttgtaaggca tgttgctaac tcatcgttac catgttgcaa gactacaaga gtattgcata   5820
agactacatt tctagatggg gggctataaa agggggtggg ggcgttcgat gcggctctgc   5880
atcccgcagg tgctgttggc cttgttcctt tccatgctga cagggccggg agaaggcagc   5940
tacccttacg atgtacctga ttacgcccaa gtgcagcttc agcagagcgg cgctgagctg   6000
gcccgcccg gggcctctgt gaaaatgagc tgcaaggctt ccggttacac ctttacaagg    6060
tacacaatgc actgggtgaa gcagcggcca gggcagggc  tagagtggat cggctacata   6120
aacccatctc ggggatatac aaactacaat caaaagttca agacaaggc cacactgaca    6180
acggacaagt caagcagcac agcttacatg caactgtcat ctctgacatc cgaggatagc   6240
gccgtttact attgcgccag atactatgat gaccactact gcttggacta ctggggacag   6300
ggaacaaccc tcacagttag ctccggcggg gggggcagtg gaggtggagg atctgggggc   6360
ggcggtagtc agatcgtcct cacacagtct ccggccataa tgtccgcctc ccccggagag   6420
aaggttacta tgacatgttc cgcatcttcc tctgtgtcat atatgaattg gtatcagcag   6480
aagagtgcca cctctcctaa acgctggatt tacgatacct ctaaactggc gtccggggtg   6540
cctgcacatt tcagaggatc aggctccggt acgagttatt cactcacaat atctgaatg    6600
gaggccgaag atgccgctac ttactactgc caacaatggt caagcaaccc cttcactttc   6660
gggagcggga caaagctgga gatcaacatg gcctcctctg gtatgtcct  ccaggcgaa    6720
ctctcccct caactgagaa ctcaagtcaa ctggacttcg aagatgtatg gaactcttcc    6780
tatggtgtga atgattcctt cccagatgga gactatgatc ccaacctgga agcagcagcc   6840
ccctgccact cctgtaacct gctggatgac tctgcactgc ccttcttcat cctcaccagt   6900
gtcctgggta tcctagctag cagcactgtc ctcttcatgc ttttcagacc tctcttccgc   6960
tggcagctct gccctggctg gcctgtcctg cacaactgc  ctgtgggcag tgccctcttc   7020
agcattgtgg tcccgtcttg gccccaggg  ctaggtagca ctcgcagctc tgccctgtgt   7080
agcctgggct actgtgtctg gtatggctca gcctttgccc aggctttgct gctaggctgc   7140
catgcctccc tgggccacag actgggtgca ggccaggtcc caggcctcac cctggggctc   7200
actgtgggaa tttggggagt ggctgcccta ctgacactgc ctgtcaccct ggccagtggt   7260
gcttctggtg gactctgcac cctgatatac agcacgagc  tgaaggcttt gcaggccaca   7320
cacactgtag cctgtcttgc catctttgtc ttgttgccat tggtttttt  gtgagccagg   7380
gggctgaaga aggcattggg tatggggcca ggccccgga  tgaatatcct gtgggcctgg   7440
tttatttct gtggcctca tggggtggtt ctaggactgg atttcctggt gaggtccaag     7500
ctgttgctgt tgtcaacatg tctgcccag caggctctgg acctgctgct gaacctggca    7560
gaagccctg  caatttgca ctgtgtggct acgcccctgc tcctgccct  attctgccac    7620
caggccaccc gcacctctt ccctctctg ccctaccctg aaggatgtc  ttctcatctg    7680
gacacccttg gaagcaaatc ctaacgactg tgccttctag ttgccagcca tctgttgttt   7740
gccctccc  cgtgccttcc ttgacccctgg aaggtgccac tccactgtc ctttcctaat    7800
aaaatgagga aattgcatcg cattgtctga gtaggtgtca ttctattctg gggggtgggg   7860
tggggcagga cagcaagggg gaggattggg aagacaatag caggaatgct ggggatgcgg   7920
tgggctctat ggatcggatc ccgggcccgt cgactgcaga ggcctgcatg caagcttggg   7980
```

-continued

```
agccagttag attgcatgtg atcgttggga atgaccccg gggttataaa aggcgcgtcc    8040
cgtggacgcg gccctcggtt gggcgacgca tgccagccca acaaaatccg ccggggtgcc    8100
agtcccattc ccgaaggcgt agcccgttaa cttggctggc ttggatgggg agtagggcct    8160
tttccattac cccaaggacc tagcgcgcgg gagtcgtggc tttggggcgc atccatggct    8220
tcggaggcgg cgcaacccga cgcgggttta tggagcgcgg ggaacgcgtt tgctgatccc    8280
ccgccccct acgatagctt gtctggtagg aacgaggggc cgtttgtcgt tattgatctg     8340
gacacccca cggacccacc tccaccgtac tctgctgggc ccctgttgtc cgtgccaatt    8400
ccgccaacct cctccggaga gggcgaggcg tcggagcggg gccgctcacg ccaagccgcc    8460
cagcgagccg ctcggcgcgc ccggcgccgc gccgaacgac gtgcgcagcg ccggagtttt    8520
ggccctggcg ggttattggc aacccccctg tttcttccgg aaaccaggct tgtggcccca    8580
cccgacatca caagggacct cttgtcgggc ctcccgacgt acgccgaggc tatgtcggac    8640
cacccccaa cctatgccac tgtcgtggcc gttcgttcga ccgaacagcc gtccggggct    8700
ttggcgcccg acgaccagcg acgaacgcaa aact                               8734
```